(12) United States Patent
Eidenberger

(10) Patent No.: US 7,862,840 B2
(45) Date of Patent: Jan. 4, 2011

(54) KIWI EXTRACT

(75) Inventor: Thomas Eidenberger, Steyr (AT)

(73) Assignee: Omnica GmbH, Hamburg (DE)

( * ) Notice: Subject to any disclaimer, the term of this patent is extended or adjusted under 35 U.S.C. 154(b) by 195 days.

(21) Appl. No.: 11/740,583

(22) Filed: Apr. 26, 2007

(65) Prior Publication Data

US 2007/0259059 A1   Nov. 8, 2007

(51) Int. Cl.
*A61K 36/00* (2006.01)

(52) U.S. Cl. .................................................. 424/777

(58) Field of Classification Search .................. None
See application file for complete search history.

(56) References Cited

U.S. PATENT DOCUMENTS

| | | | |
|---|---|---|---|
| 4,921,475 A | 5/1990 | Sibalis | |
| 5,008,110 A | 4/1991 | Benecke et al. | |
| 5,053,232 A | 10/1991 | Balestrieri et al. | |
| 5,087,240 A | 2/1992 | Sibalis | |
| 5,088,977 A | 2/1992 | Sibalis | |
| 5,163,899 A | 11/1992 | Sibalis | |
| 5,164,189 A | 11/1992 | Farhadieh et al. | |
| 5,254,346 A | 10/1993 | Tucker et al. | |
| 5,290,561 A | 3/1994 | Farhadieh et al. | |
| 5,332,213 A | 7/1994 | Klose | |
| 5,336,168 A | 8/1994 | Sibalis | |
| 5,352,456 A | 10/1994 | Fallon et al. | |
| 5,407,713 A | 4/1995 | Wilfong et al. | |
| 6,054,169 A * | 4/2000 | Gauthie-Jaques et al. | 426/599 |
| 6,605,296 B1 * | 8/2003 | Stuckler | 424/439 |
| 7,118,882 B2 * | 10/2006 | Banerjee et al. | 435/42 |
| 2002/0054923 A1 * | 5/2002 | Suzuki et al. | 424/729 |
| 2003/0045473 A1 * | 3/2003 | Sarama et al. | 514/12 |
| 2003/0147938 A1 | 8/2003 | Hirsch | |
| 2004/0037909 A1 * | 2/2004 | Kim et al. | 424/769 |

FOREIGN PATENT DOCUMENTS

| | | |
|---|---|---|
| CN | 1156624 A | 8/1997 |
| CN | 1362025 A | 8/2002 |
| CN | 1539986 | 10/2004 |
| CN | 1560243 | 1/2005 |
| EP | 0 359 822 A1 | 3/1990 |
| JP | 6-1140510 | 6/1986 |
| JP | 2-072850 | 3/1990 |
| JP | 2202808 A | 8/1990 |
| JP | 04278063 A * | 10/1992 |
| JP | 6-256207 | 9/1994 |
| JP | 11246428 | 9/1999 |
| JP | 2001151696 | 7/2001 |
| JP | 2002-293780 | 10/2002 |
| JP | 2003/061615 A | 3/2003 |
| JP | 2003-171294 | 5/2008 |
| KR | 10-2001-0096881 | 8/2001 |
| KR | 20040080640 | 9/2004 |
| KR | 20040097716 | 11/2004 |
| WO | WO 91/03172 | 3/1991 |
| WO | WO 01/70259 | 9/2001 |
| WO | WO 03003415 | 1/2003 |
| WO | WO 2004/017982 | 3/2004 |
| WO | WO 2005/096849 | 10/2005 |
| WO | WO 2005/5096840 | * 10/2005 |
| WO | WO 2005/110404 | 11/2005 |
| WO | WO 2006/016728 | 2/2006 |

OTHER PUBLICATIONS

Alberts et al. "The Condensation Reaction of Patty Acid Synthesis" J Biol Chem (1963) 238:557-65.
Alo et al. "Fatty Acid Synthase (FAS) Predictive Strength in Poorly Differentiated Early Breast Carcinomas" Tumori (1999) 85(1): 35-40.
Balestrieri et al. "A glycoprotein inhibitor of pectin methylesterase in kiwi fruit (*Actinidia chinesis*)" Eur. J. Biochem. (1990) 193:183-187.
Banerjee et al. "inhA, a Gene Encoding a Target for Isoniazid and Ethionamide in *Mycobacterium tuberculosis*" Science (1994) 263(5144):227-30.
Beecher GR "Overview of Dietary Favonoids: Nomenclature, Occurrence and Intake" J. Nutr. (2003) 133: 3248S-3254S.
Benzie et al. "Total Antioxidant Capacity of Teas by the Ferric Reducing/Antioxidant Power Assay" J. Agric Food Chem. (1999) 47: 633-636.
Bressler et al. "Studies of the Mechanism of Fatty Acid Synthesis" J Biol Chem (1961) 236:1643:51.
Brooks et al. "Fat Metabolism in Higher Plants" Arch Biochem Biophys (1966) 116:108-16.
Brusselmans et al. "Induction of Cancer Cell Apoptosis by Favonoids is Associated with Their Ability to Inhibit Fatty Acid Synthase Activity" JBC (2005) 280(7): 5636-5645.
Burton et al. (1968) "Comparative Studies of the Rat and Pigeon Liver Fatty Acid Synthetases" Arch Biochem Biophys 126:141-154.
Butterworth et al. "The Partial Dissociation and the Reassociation of the Pigeon Liver Fatty Acid Synthetase Complex" J Biol Chem (1967) 242:3508-16.
Coulston et al. "Persistence of Hypertriglyceridemic Effect of Low-Fat High-Carbohydrate Diets in NIDDM Patients" Diabetes Care (1989) 12(2):94-101.
Danforth E Jr. "Diet and obesity" Am J Clin Nutr (1985) 41(5 Suppl): 1132-45.
Deters et al. "Kiwi Fruit (*Actinidia chinensis* L.) Polysaccharides Exert Stimulating Effects on Cell Proliferation via Enhanced Growth Factor Receptors, Energy Production, and Collagen Synthesis of Human Keratiniocytes, Fibroblasts, and Skin Equivalents" J. Cell. Physiol (2005) 202: 717-722.

(Continued)

Primary Examiner—Christopher R. Tate
Assistant Examiner—Deborah A. Davis
(74) Attorney, Agent, or Firm—Scott D. Rothenberger; Colin L. Fairman; Fulbright & Jaworski

(57) ABSTRACT

The invention describes the preparation, isolation and use of an extract of kiwi fruit for the treatment of a disease or condition related with, caused by or mediated by activity of human pancreatic lipase and/or human fatty acid synthase.

14 Claims, 15 Drawing Sheets

OTHER PUBLICATIONS

Diraison et al. "Role of human liver lipogenesis and reesterification in trigylcerides secretion and in FFA reesterification" Am. J. Physiol (1998) 274:E321-7.

Epstein et al. "OA-519 (Fatty Acid Synthase) as an Independent Predictor of Pathologic Stage in Adenocarcinoma of the Prostate" Urology 1995 45(1):81-6.

Fujiki et al. "Cancer inhibition by green tea" Mutat. Res. (1998) 402: 307-310.

Gansler et al. "Increased Expression of Fatty Acid Synthase (OA-519) in Ovarian Neoplasms Predicts Shorter Survival" Hum Pathol (1997) 28(6) 686-92.

Hayashi et al. "Inhibition of Fatty Acid Synthesis by the Antibiotic Thiolactomycin" Antibiot (Tokyo) (1984)37(11):1456-61.

Heath et al. "Broad Spectrum Antimicrobial Biocides Target the FabI Component of Fatty Acid Synthesis" J Biol Chem (1998) 273(46): 30316-20.

Hellerstein et al. "Measurement of De Novo Hepatic Lipgenesis in Humans Using Stable Isotopes" J Clin Invest (1991) 87(5): 1841-52.

Hollenbeck et al. "Effects of Dietary Carbohydrate and Fat Intake on Glucose and Lipoprotein Metabolism in Individuals with Diabetes Mellitus" Diabetes Care (1989) 14(9): 774-85.

Ikeda et al. "Tea catechins decrease micellar solubility and intestinal absorption of cholesterol in rats" Biochim. Biophys. Acta (1992) 1127: 141-146.

Ikeda et al. "Heat-Epimerized Tea Catechins Rich in Gallocatechin Gallate and Catechin Gallate are more effective to inhibit choelsterol absorption than Tea Catechins Rich in Epigallocatechin Gallate and Epicatechin Gallate" J. Agric. Food Chem. (2003) 51:7303-7307.

Imeh et al. "Distribution of Conjugated and Free Phenols in Fruits" Antioxidant Activity and Cultivar Variations J. Agric Food Chem (2002) 50: 6301-6306.

Karamac et al. "Inhibition of Pancreatic Lipase by Phenolic Acids—Examination in vitro"Z. Naturforsch (1996) 51c: 903-905.

Kuhajda et al. "Synthesis and antitumor activity of an inhibitor of fatty acid synthase" Proc Natl Acad Sci (2000) 97:3450-54.

Laakso et al. "CT2108A and B: New Fatty Acid Synthase Inhibitors as Antifungal Agents" J Nat Prod (2003) 66(8): 1041-6.

Li et al. "Inhibitory Effects of Flavonoids on Animal Fatty Acid Synthase" J Biochem (2004) 135:85-91.

Loftus et al. "Reduced Food Intake and Body Weight in Mice Treated with Fatty Acid Synthase Inhibitors" Science (2000) 288(5475):2379-81.

McMurry et al. "Triclosan targets lipid synthesis" Nature (1998) 394(6693):531-2.

Milgraum et al. "Enzymes of the Fatty Acid Synthesis Pathway are Highly Expressed in in Situ Breast Carcinoma" Clin Cancer Res (1997) 3(11):2115-20.

Miura et al. "The Inhibitory Effects of Tea Polyphenols (Flavan-3-ol Derivatives) on Cu2+ Mediated Oxidative Modifcation of Low Density Lipoprotein" Biol Pharm. Bull. (1994) 17:1567-1572.

Murase et al. "Beneficial effects of Tea catechins on diet-induced obesity: Stimulation of lipid catabolism in the iver" Int. J. Obesity (2002) 26: 1459-1464.

Nakai et al. "Inhibitory Effects of Oolong Tea Polyphenols on Pancreatic Lipase in Vitro" J. Agric. Food Chem. (2005) 53: 4593-4598.

Pizer et al. "Fatty Acid Synthase Expression in Endometrial Carcinoma" Cancer (1998) 83(3):528-37.

Pizer et al. "Inhibition of Fatty Acid Synthesis Induces Programmed Cell Death in Human Breast Cancer Cells" Cancer Res (1996) 56(12):2745-7.

Rashid et al. "Elevated Expression of Fatty Acid Synthase and Fatty Acid Synthetic Activity in Colorectal Neoplasia" Am J Pathol (1997) 150(1): 201-8.

Shurbaji et al. (1996) "Immunohistochemical Detection of a Fatty Acid Synthase (OA-519) as a Predictor of Progression of Prostate Cancer" Hum Pathol (1996) 27(9): 917-21.

Singleton et al. "Analysis of Total Phenols and Other Oxidation Substrates and Antioxidants by Means of Folin-Ciocalteu Reagent" Methods Enzymol (1999) 299:152-178.

Smith S. "The animal fatty acid synthase: one gene, onepolypeptide, seven enzymes" FASEB (1994)8:1248-59.

Suzuki et al. "Inhibitory Activities of (—) —Epigallocatechin-3-O-gallate against Topoisomerases I and II" Biol. Pharm. Bull. (2001) 24: 1088-1090.

Vance et al. "Inhibition of Fatty Acid Synthetases by the Antibiotic Cerulenin" Biochem Biophys Res Commun (1972) 48:649-56.

Vinson et al. "Phenol Antioxidant Quantity and Quality in Foods: Fruits" J. Agric. Food Chem (2001) 49:5315-5321.

Wakil, S. "Fatty Acid Synthase, A Proficient Multifunctional Enzyme" Biochemistry (1989) 28:4523-30.

Wang et al. "Green Tea Epigallocatechin Gallate" A Natural Inhibitor of Fatty-Acid Synthase Biochem Biophys Res Commun (2001) 288:1200-06.

Yang et al. "Tea and Cancer" J. Natl. Cancer Inst. (1993) 85: 1038-1049.

Yen et al. "Antioxidant Activity of Various Tea Extracts in Relation to Their Antimultagenicity" Agric. Food Chem. (1995) 43:27-32.

Zhang et al. "Evaluation of Epigallocatechin Gallate and Related Plant Polyphenols as Inhibitors of the FabG and FabI Reductases of Bacterial Type II Fatty-acid Synthase" J. Biological Chemistry (2004) 279(30): 30094-31001.

Takano, Fumihide et al., "Isolation of (+)-Catechin and (−)-Epicatechin from *Actinidia arguta* as Bone Marrow Cell Proliferation Promoting Compounds," Planta Medica, vol. 69, No. 4, Apr. 2003, pp. 321-326, XP002514188, ISSN: 0032-0943.

International Search Report (4 pgs.).

* cited by examiner

KIWI EXTRACT

CROSS REFERENCE TO RELATED APPLICATIONS

This application claims priority to Austrian Patent Application No. A778/2006 filed on May 5, 2006, the contents of which are incorporated in by reference.

FIELD OF THE INVENTION

The invention relates generally to methods isolate and purify kiwi extracts and related compositions.

BACKGROUND OF THE INVENTION

Polyphenols are widely distributed in plants and a major class of secondary plant products. More than 5000 different polyphenols have been identified and the estimated number of polyphenols in nature is most likely much higher than that due the complexity of the class of compounds. In general polyphenols are found in plants as free polyphenol monomers (e.g. flavanols, flavanons, flavons, anthocyanidins) or as conjugated tannins such as hydrolyzable tannins, derived tannins or condensed tannins and proanthocyanidins.

Many health benefits of tea, fruits and vegetables are attributed to polyphenols. For example, green tea polyphenols, are valued due to their proven antioxidative, antimutagenic, anticarcinogenic and hypocholesteremic effects as well as their potential to prevent cardiovascular diseases.

Tea polyphenols are generally well characterised in the literature. It has been reported that 200 ml green tea contains up to 140 mg (−)-epigallocatechin gallate (EGCG), 65 mg (−)-epigallocatechin (EGC), 28 mg (−)-epicatechin gallate (ECG) and 17 mg (−)-epicatechin. The high content of galloyl-units was shown to be correlated with apoptosis induced in prostate and breast cancer cells and the inhibition of the fatty acid synthase enzyme.

The enzyme fatty acid synthase (FAS) is an important enzyme that is involved in energy metabolism in-vivo and has been shown to be related to various human diseases.

Based on investigations, two enzyme systems have been identified that are referred to as types 1 and 2. Type 1 FAS is found in higher animals and yeasts whereas type 2 occurs predominantly in plants and bacteria. Animal FAS is composed of two identical multifunctional polypeptide chains, each containing six discrete functional domains with enzymatic activity. FAS synthesizes de-novo mainly palmitinic acid from the substrates acetyl-coenzyme A (Ac-CoA), malonyl-coenzyme A (Mal-CoA) and NADPH according to following reaction scheme:

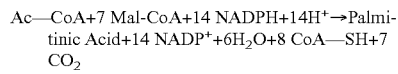

FAS is located in most animal tissues and in high amounts in the liver. Under normal conditions FAS activity in tissue is down-regulated due to sufficient dietary fat available. In various pathophysiological conditions, i.e. malignancies in colon, prostate, breast, endometrium or ovary carcinoma, the FAS activity was shown to be up-regulated to surprisingly high levels. Hence, inhibition of FAS that was found to be associated with reduction of tumour growth and apoptosis of malignant cells, might serve as a valuable target for treatment of cancer.

Recent studies also showed that FAS inhibition can reduce food intake and body weight in mice. It was further shown that de-novo lipogenesis in humans via the FAS contributes to circulating triglycerides levels. Together with re-esterification of free fatty acids in plasma it contributes to around 50% of the triglyceride levels whereas the remaining 50% are stemming from the breakdown and absorption of dietary lipoproteins and from fat stores in the body.

It should be noted that lipogenesis studies in healthy, non-obese humans suggest that lipogenesis via the FAS system is not a major pathway in terms of conversion and secretion to triglycerides. Therefore, inhibition of the FAS in healthy, non-obese humans is considered generally not to be an effective way to reduce the fat content in the body. However, from studies in mice it was concluded that inhibitors of the FAS are also responsible for a reduced food intake and for body weight loss that could be attributed to fat loss.

Moreover, studies in obese humans and patients suffering from diabetes indicate that hypertriglyceridema is strongly associated with carbohydrate intake most likely to be due to conversion of metabolites of the glycolysis to lipids via de novo lipogenesis.

Obesity is caused by the results of an imbalance between energy intake and expenditure. Excess energy is stored in fat cells that enlarge or increase in number. Moreover, obesity is a strong risk factor for various diseases, such as hypertension, hyperlipidemia, arteriosclerosis, and diabetes. Therefore, an effective way to prevent obesity is to inhibit fat absorption from intestine.

Pancreatic lipase is a key enzyme for lipid absorption. It is known that dietary fat is not directly absorbed from the intestine unless it has been subjected to the action of pancreatic lipase. Thereby, to suppress weight gain, it would be effective to reduce fat absorption by lipase inhibition.

Therefore, a need exists for composition that can help alleviate one or more of these pervasive conditions and/or method that provide suitable compositions, particularly from naturally occurring sources.

BRIEF SUMMARY OF THE INVENTION

The present invention surprisingly provides isolated kiwi extracts that have greater than about 10% by weight of one or more conjugated polyphenolic derivative(s). These polyphenolic derivatives are derived from the monomeric subunits of gallic acid derivatives, caffeic acid derivatives and catechin derivatives or mixtures thereof.

The isolated extract can optionally include a binder, such as a cyclodextrin as a carrier.

The present invention also pertains to methods of preparing the kiwi extracts described herein.

The present invention further pertains to methods of treatment of various ailments by administration of a therapeutically effective amount of the kiwi extracts described herein.

In one aspect, the present invention provides a method of treatment of diseases or conditions related with or caused by activity of human pancreatic lipase (LPS) and/or human fatty acid synthase (FAS).

Therefore, the present invention further provides bioavailable conjugated polyphenolic derivatives in therapeutic levels from kiwi extracts described herein.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
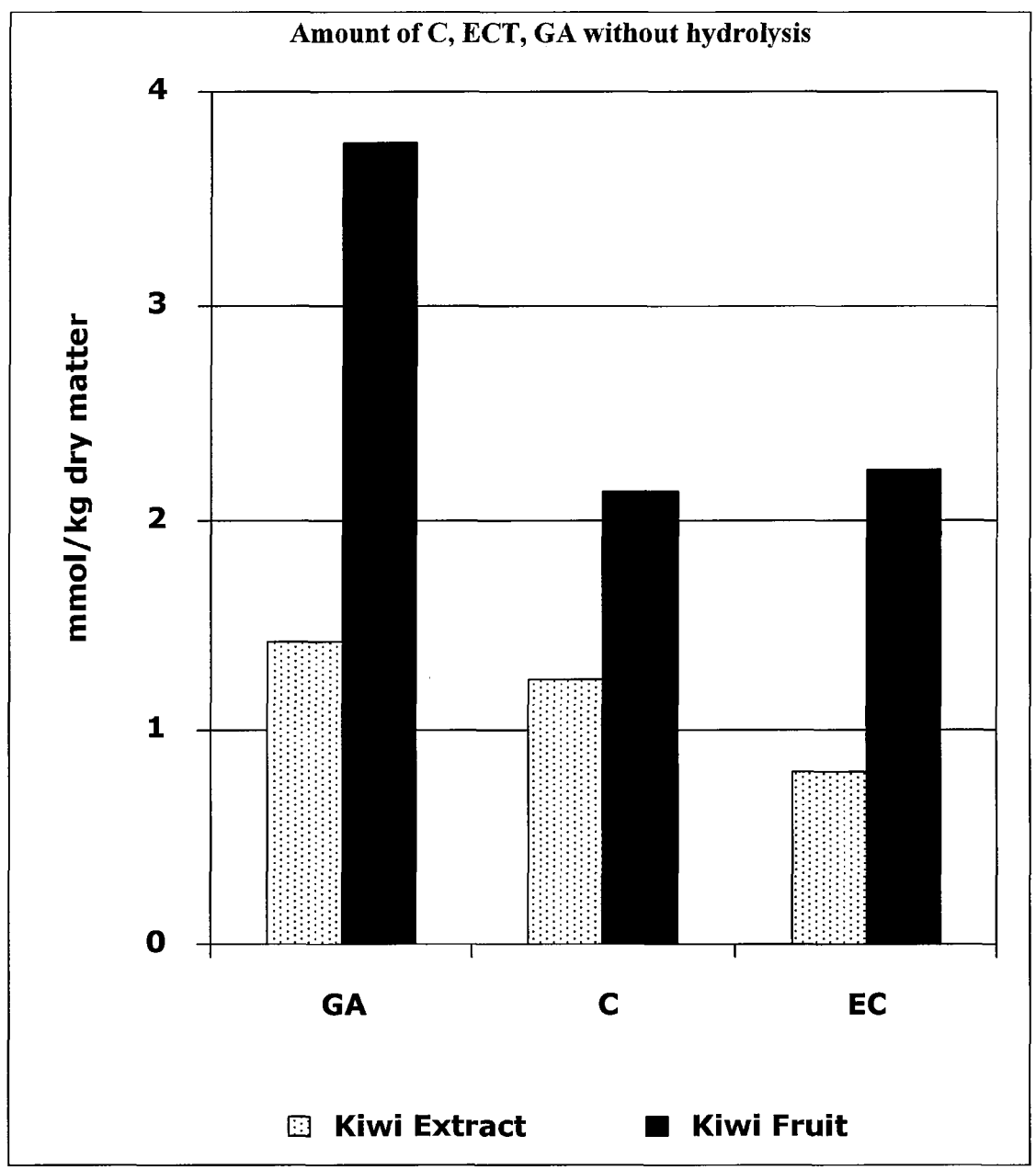
FIGS. 1 and 2 show the amount of Catechin (C), Epicatechin (EC) and Gallic Acid (GA) in samples of fresh Kiwi fruit and Kiwi fruit extract, obtained with or without hydrolysis of the polyphenols, respectively.

The present invention relates to kiwi extract that have enhanced content, by weight, of conjugated polyphenolic materials that are not found at such levels in naturally occurring kiwi sources.

In the specification and in the claims, the terms "including" and "comprising" are open-ended terms and should be interpreted to mean "including, but not limited to . . ." These terms encompass the more restrictive terms "consisting essentially of" and "consisting of."

Various sources of kiwi fruit are acceptable. Although not to be limited by the following, the kiwi fruit can be ideally obtained from Actinidia Chinensis or Actinidia Deliciosa fruit.

The term "extract" is intended to mean kiwi compositions obtained from plant sources, such as leaves, twigs, bark, roots, stem, seeds, flowers, berries, fruit, for example, by isolation methods described herein. It has been surprisingly found that extract of kiwi material provides an extract that has an enhanced weight percentage of conjugated polyphenols, as compared to kiwi fruit per se or as a freeze dried product. Ideally, the pulp and the juice of the kiwi fruit are used.

The kiwi fruit extract is generally obtained with a solvent selected from aliphatic alcohols, e.g., ethanol; acetone, hexane, chloroform, ethyl acetate, petroleum ether, mixtures thereof and/or mixtures thereof with water. In particular, an ethanolic extract of kiwi fruit can be prepared with ethanol or with a mixture of ethanol and water.

In accordance with the present invention, the isolated kiwi extract contains one or more conjugated polyphenols derived from galleic acid derivatives, caffeic acid derivatives, catechin derivatives and mixtures thereof. In yet another embodiment, the extract contains at least a conjugated polyphenol from a gallic acid derivative. In another embodiment, the extract contains at least a conjugated polyphenol from a caffeic acid derivative. In still yet another embodiment, the extract contains at least a conjugated polyphenol from a catechin derivative.

The term gallic acid derivative is intended to include gallic acid, dihydroxybenzoic acid and p-hydroxybenzoic acid.

The term caffeic acid derivative is intended to include caffeic acid, coumaric acid and ferulic acid.

The term catechin derivative is intended to include catechin and gallocatechin.

In one aspect, the isolated kiwi extract to the present invention provides 75% or more, 90% or more and even 95% or more polyphenols (such as gallic acid derivatives, caffeic acid derivatives or catechin derivatives) as conjugated tannins.

Oligo- and polymeric polyphenols are differentiated by their stability. Polyphenols which are hydrolyzed to the basic structures in hot water are referred to as hydrolyzable tannins. Polyphenols which are hydrolyzed only in presence of strong acids are referred to as derived or condensed tannins.

Polyphenols occur in "free" (monomeric) and "conjugated" (oligo-/polymeric) forms.

In another aspect, the isolated kiwi extract according to the present invention contains Catechin (C) and Gallic Acid (GA). The catechin and gallic acid present in the extract are present in a conjugated form in an amount of 75% or more, 90% or more, and even 95% or more, respectively.

The present invention provides that conjugated tannins exhibit a higher inhibiting effect towards LPS and FAS than free polyphenols. Therefore, kiwi extracts containing increased amounts of conjugated tannins were found to have a very good inhibiting activity with respect to LPS and FAS.

The isolated kiwi extracts of the present invention can be utilized in the treatment of a disease including metabolic disorders, such as obesity, hyperlipidemia, hypertension, arteriosclerosis, diabetes, Taxation, constipation, fatty liver disease; and cancer, such as colon, prostate, breast, endometrium or ovary carcinoma. These diseases have been shown to be linked to the activity of LPS and/or FAS.

In one exemplary method, the kiwi extract of the present invention can be isolated by a process generally comprising the steps:

Juice is pressed out of fresh kiwi fruit. The residue after filtration is used as a raw material or dried fruit is used as raw material.

Extraction: The raw material, from pressing the fresh kiwi or from dried kiwi fruit, is extracted using from about three to about five times the weight of the raw material with from about 40 to about 90 wt. % ethanol, e.g. 50, 60, 70 or 80 wt % (remainder water) at room temperature. The mixture is stirred for about 1 to about 6 hours, e.g., 3 hours, and then filtered via gravity filtration, by pressing or by centrifugation. The raw material is extracted about one or two more times, as above, with about three to about five times the weight of the raw material, filtered, and then the extracts are combined.

Concentration: The extracted solution is then concentrated at a temperature about below 45° C. under reduced pressure (approximately between about −0.09 to about −0.08 Mpa) to provide an extract concentrate. Lower temperatures are preferred, with temperature ranges for the concentration being from about room temperature to about 45° C., e.g., 30, 35 or 40° C.

Optional coating: An excipient, such as a dextrin (beta-cyclodextrin) or another starch derivative can be added to the extract concentrate. The solution can be stirred until the derivative is fully dissolved.

Optional spray-drying: A powder of coated isolated kiwi extract can be obtained by spray-drying.

Alternatively, the extract concentrate can be concentrated at reduced pressure at a temperature below about 45° C., as described above, until a dried powder is obtained.

Typically the isolated kiwi extract is concentrated by various methods to provide a solution enriched in conjugated polyphenols. For example, ultrafiltration can be used to remove unwanted components by molecular weight cut offs. The retentate from the filtration can be stored as a liquid or, for example, can then be further concentrated into a powder by spray drying, freeze drying, flash drying, fluidized bed drying, ring drying, tray drying, vacuum drying, radio frequency drying or microwave drying. Ultimately, the extract should contain at least 10% by weight conjugated polyphenolic content. The extracts, therefore, contain conjugated polyphenolic derivatives and, optionally, other plant materials such as other flavinoids, sugars, etc.

The kiwi extracts can be further purified by one or more methods known in the art, such as chromatography, gel chromatography, high performance liquid chromatography, crystallization, affinity chromatography, partition chromatography and the like. Identification of the particular polyphenol(s) can be accomplished by methods know to those skilled in the art and include $^1$H NMR, chemical degradation, chromatography and spectroscopy, especially homo- and heteronuclear two-dimensional NMR techniques for the characterization of the isolated polyphenolic compounds.

The term "purified" or "isolated" is used in reference to the purification and/or isolation of one or more polyphenolic compounds from a kiwi extract as described above. Again using conventional methods known in the art, various components of the kiwi extract can be separated into purified materials. In one aspect of the invention, the polyphenol(s) of the extract are substantially purified and isolated by techniques known in the art. The purity of the purified compounds is generally at least about 90%, preferably at least about 95%, and most preferably at least about 99% and even more preferably at least about 99.9% (e.g. about 100%) by weight.

Therefore, the present invention further provides bioavailable isolated kiwi extract compositions described herein that are useful to treat various afflictions noted herein. The kiwi extract can be administered by a number of methods, as discussed infra.

The compositions of the invention can be incorporated into various foods, drinks, snacks, etc. In one aspect, the composition can be sprinkled onto a food product, prior to consumption. If sprinkled onto a food product, a suitable carrier such as starch, sucrose or lactose, can be used to help distribute the concentration of the kiwi extract making it easier to apply to the food product.

The compositions of the present invention can also be provided as supplements in various prepared food products. For the purposes of this application, prepared food product means any natural, processed, diet or non-diet food product to which a composition of the invention has been added. The compositions of the present invention can be directly incorporated into many prepared diet food products, including, but not limited to diet drinks, diet bars and prepared frozen meals. Furthermore, the compositions of the inventions can be incorporated into many prepared non-diet products, including, but not limited to candy, snack products such as chips, prepared meat products, milk, cheese, yogurt, sport bars, sport drinks, mayonnaise, salad dressing, bread and any other fat or oil containing foods. As used herein, the term "food product" refers to any substance fit for human or animal consumption.

The compositions of the invention can be added to various drinks, such as fruit juices, milkshakes, milk, etc.

The preferred method of administration is oral. The compositions of the invention can be formulated with suitable carriers such as starch, sucrose or lactose in tablets, capsules, solutions, syrups and emulsions. The tablet or capsule of the present invention can be coated with an enteric coating that dissolves at a pH of about 6.0 to 7.0. A suitable enteric coating, which dissolves in the small intestine but not in the stomach, is cellulose acetate phthalate.

Formulation of the compositions of the invention into a soft gel capsule can be accomplished by many methods known in the art. Often the formulation will include an acceptable carrier, such as an oil, or other suspending or emulsifying agent.

Suitable optional carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, wheat germ oil, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The formulations of the invention are also considered to be nutraceuticals. The term "nutraceutical" is recognized in the art and is intended to describe specific chemical compounds found in foods that can prevent disease or ameliorate an undesirable condition.

The formulations of the invention can further include various ingredients to help stabilize, or help promote the bioavailability of the components of the beneficial compositions of the invention or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals can be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Various additives can be incorporated into the present compositions. Optional additives of the present composition include, without limitation, hyaluronic acid, phospholipids, starches, sugars, fats, antioxidants, amino acids, proteins, flavorings, coloring agents, hydrolyzed starch(es) and derivatives thereof or combinations thereof.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, camosic acid and rosmanol found in rosemary and hawthorn extract, proanthocyanidins such as those found in grapeseed or pine bark extract, and green tea extract.

Compositions comprising the kiwi extract compositions of the invention can be manufactured by methods of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries that facilitate processing of the stabilized kiwi extract compositions into preparations that can be used.

The compositions of the invention can take a form suitable for virtually any mode of administration, including, for example, oral, buccal, systemic, injection, transdermal, rectal, vaginal, etc., or a form suitable for administration by inhalation or insufflation.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the kiwi extract compositions in aqueous or oily vehicles. The compositions can also contain formulating agents, such as suspending, stabilizing and/or dispersing agent. The formulations for injection can be presented in unit dosage form, e.g., in ampoules or in multidose containers, and can contain added preservatives.

Alternatively, the injectable formulation can be provided in powder form for reconstitution with a suitable vehicle, including but not limited to sterile pyrogen free water, buffer, dextrose solution, etc., before use. To this end, the kiwi extract compositions can be dried by any art-known technique, such as lyophilization, and reconstituted prior to use.

For transmucosal administration, penetrants appropriate to the barrier to be permeated are used in the formulation. Such penetrants are known in the art.

For oral administration, the compositions of the invention can take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars, films or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

Preparations for oral administration can be suitably formulated to give controlled release of the kiwi extract composition as is well known.

For buccal administration, the compositions can take the form of tablets or lozenges formulated in conventional manner.

For rectal and vaginal routes of administration, the kiwi extract compositions can be formulated as solutions (for retention enemas) suppositories or ointments containing conventional suppository bases such as cocoa butter or other glycerides.

For nasal administration or administration by inhalation or insufflation, the kiwi extract compositions can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

For prolonged delivery, the kiwi extract compositions can be formulated as a depot preparation for administration by implantation or intramuscular injection. The kiwi extract compositions can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch, which slowly releases the kiwi extract compositions for percutaneous absorption, can be used. To this end, permeation enhancers can be used to facilitate transdermal penetration of the kiwi extract compositions. Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other delivery systems can be employed. Liposomes and emulsions are well-known examples of delivery vehicles that can be used to deliver kiwi extract compositions. Certain organic solvents such as dimethylsulfoxide (DMSO) can also be employed, although usually at the cost of greater toxicity.

The compositions can, if desired, be presented in a pack or dispenser device, which can contain one or more unit dosage forms containing the kiwi extract compositions. The pack can, for example, comprise metal or plastic foil, such as a blister pack. The pack or dispenser device can be accompanied by instructions for administration.

Soft gel or soft gelatin capsules can be prepared, for example, without limitation, by dispersing the formulation in an appropriate vehicle (e.g., rice bran oil, and/or beeswax) to form a high viscosity mixture. This mixture is then encapsulated with a gelatin based film using technology and machinery known to those in the soft gel industry. The capsules so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally a carrier such as rice bran oil or wheat germ oil and/or beeswax if desired) and can include, apart from the kiwi extract compositions, a hydrophilic matrix. The hydrophilic matrix, if present, is a polyethylene glycol having an average molecular weight of from about 200 to 1000. Further ingredients are optionally thickening agents and/or emulsifying agent(s). In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes is mature technologies and is all widely available to any one wishing to prepare soft gelatin capsules.

Emulsifying agents can be used to help solubilize the ingredients within the soft gelatin capsule. Specific examples of the surfactant, emulsifier, or effervescent agent include D-sorbitol, ethanol, carrageenan, carboxyvinyl polymer, carmellose sodium, guar gum, glycerol, glycerol fatty acid ester, cholesterol, white beeswax, dioctyl sodium sulfosuccinate, sucrose fatty acid ester, stearyl alcohol, stearic acid, polyoxyl 40 stearate, sorbitan sesquioleate, cetanol, gelatin, sorbitan fatty acid ester, talc, sorbitan trioleate, paraffin, potato starch, hydroxypropyl cellulose, propylene glycol, propylene glycol fatty acid ester, pectin, polyoxyethylene (105) polyoxypropylene (5) glycol, polyoxyethylene (160) polyoxypropylene (30) glycol, polyoxyethylene hydrogenated castor oil, polyoxyethylene hydrogenated castor oil 40, polyoxyethylene hydrogenated castor oil 60, polyoxyl 35 castor oil, polysorbate 20, polysorbate 60, polysorbate 80, macrogol 400, octyldodecyl myristate, methyl cellulose, sorbitan monooleate, glycerol monostearate, sorbitan monopalmitate, sorbitan monolaurate, lauryl dimethylamine oxide solution, sodium lauryl sulfate, lauromacrogol, dry sodium carbonate, tartaric acid, sodium hydroxide, purified soybean lecithin, soybean lecithin, potassium carbonate, sodium hydrogen carbonate, medium-chain triglyceride, citric anhydride, cotton seed oil-soybean oil mixture, and liquid paraffin.

The present invention also provides packaged formulations of the compositions of the invention and instructions for use of the product for appropriate condition(s). Typically, the packaged formulation, in whatever form, is administered to an individual in need thereof. Typically, the dosage requirement is between about 1 to about 4 dosages a day.

Although the present invention describes the preparation, use, manufacture and packaging of the compositions of the invention in soft gelatin capsules for treatment of various conditions, it should not be considered limited to only soft gelatin capsules. Ingestible compositions of the invention can be delivered in traditional tablets, pills, lozenges, elixirs, emulsions, hard capsules, liquids, suspensions, etc. as described above.

The kiwi extract compositions of the invention, or compositions thereof, will generally be used in an amount effective to achieve the intended result, for example in an amount effective to treat or prevent the particular related condition being treated. The composition can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a composition of the invention to a patient suffering from pain provides therapeutic benefit not only when the underlying condition is eradicated or ameliorated, but also when the patient reports a decrease in the severity or duration of the physical discomfort associated with the pain.

For prophylactic administration, the composition can be administered to a patient at risk of developing one of the previously described conditions.

The amount of composition administered will depend upon a variety of factors, including, for example, the particular indication being treated, the mode of administration, whether the desired benefit is prophylactic or therapeutic, the severity of the indication being treated and the age and weight of the patient, etc. Determination of an effective dosage is well within the capabilities of those skilled in the art.

Total dosage amounts of a kiwi extract composition will typically be in the range of from about 0.0001 or 0.001 or 0.01 mg/kg/day to about 100 mg/kg/day, but may be higher or lower, depending upon, among other factors, the activity of the components, its bioavailability, the mode of administration and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. Skilled artisans will be able to optimize effective local dosages without undue experimentation.

The following paragraphs enumerated consecutively from 1 through 15 provide for various aspects of the present invention. In one embodiment, in a first paragraph (1), the present invention provides 1. An isolated kiwi extract comprising greater than about 10% by weight of a conjugated polyphenolic derivative.

2. The isolated kiwi extract of paragraph 1, wherein the conjugated polyphenolic derivative comprises a gallic acid derivative, a caffeic acid derivative and a catechin derivatives or mixtures thereof.

3. The isolated kiwi extract of paragraph 2, wherein the ratio of polyphenolic gallic acid derivative to polyphenolic catechin derivative is from about 1 to about 1 to about 10 to about 1.

4. The isolated kiwi extract of paragraph 2, wherein the ratio of polyphenolic caffeic acid derivative to polyphenolic catechin derivative is from about 1 to about 1 to about 10 to about 1.

5. The isolated kiwi extract of paragraph 2, wherein the ratio of polyphenolic gallic acid derivative, caffeic acid derivative and catechin derivative condensates are from about 1 to about 1 to about 1 to about 10 to about 10 to about 1.

6. The isolated kiwi extract of any of paragraphs 2 through 5, wherein the polyphenolic gallic acid derivative is gallic acid, dihydroxybenzoic acid or p-hydroxybenzoic acid, the polyphenolic caffeic acid derivative is caffeic acid, coumaric acid or ferulic acid, the polyphenolic catechin derivative is catechin or gallocatechin, or mixtures thereof.

7. The isolated kiwi extract of any of paragraphs 1 through 6, wherein the molecular weight of the conjugated polyphenolic derivative is between about 2,000 and about 4,000.

8. The isolated kiwi extract of paragraph 7, wherein the molecular weight of the conjugated polyphenolic derivative is about 3,000.

9. The isolated kiwi extract of any of paragraphs 2 through 6, wherein the degree of polymerization of the conjugated polyphenolic derivative is between about 15 and about 25.

10. The isolated kiwi extract of paragraph 9, wherein the degree of polymerization of the conjugated polyphenolic derivative is about 20.

11. The isolated kiwi extract of any of paragraphs 1 through 10, wherein 1 gram of isolated kiwi extract contains from about 500 to about 700 µmol gallic acid equivalents.

12. The isolated kiwi extract of any of paragraphs 1 through 10, wherein 1 gram of isolated kiwi extract contains from about 250 to about 400 µmol catechin equivalents.

13. Use according to any of the preceding paragraphs for the treatment of a disease comprising metabolic disorders, such as obesity, hyperlipidemia, hypertension, arteriosclerosis, diabetes, Taxation, constipation, fatty liver disease; and cancer, such as colon, prostate, breast, endometrium or ovary carcinoma.

14. A soft gelatin capsule comprising:
a soft gelatin capsule encapsulating any of the compositions of any of preceding paragraphs 1 through 12.

15. A packaged formulation comprising:
a composition of any of paragraphs 1 through 12; and
instructions for use thereof in a therapeutically effective manner to treat a disease or condition associated with metabolic disorders, such as obesity, hyperlipidemia, hypertension, arteriosclerosis, diabetes, Taxation, constipation, fatty liver disease; and cancer, such as colon, prostate, breast, endometrium or ovary carcinoma.

The following examples are not to be meant as limiting but are presented to provide additional information and support for the invention.

EXAMPLES

Example 1

Preparation of Kiwi Fruit Extract 1,000 kg fresh kiwi was ground and pressed. 350 kg of juice was obtained. 650 kg residue was obtained as raw material. 3,500 liters of 80% ethanol (aqueous ethanol) as solvent was added to the raw material at room temperature (20° C.) and the mixture was stirred for one hour. The extracted was filtered. The residue of the raw material was further extracted with 3,500 liters 80% ethanol at room temperature (21° C.) for one hour. The extracted was filtered. The two extracts were combined with the pressed juice and then concentrated to about 600 liter at 42° C. under reduced pressure (−0.085 Mpa). 12 kg Beta-cyclodextrin were added to the concentrate with stirring until the cyclodextrin was fully dissolved. 62.5 kg powder of coated Kiwi extract is obtained upon spray drying.

The extract was found to contain 5.0% actinidines with a biological activity of 113,000 IU/g. According to Folin-Ciocalteau assay methodology, the amount of total polyphenols was found to be greater than about 10% (m/m) (weight by weight), the amount of catechin (m/m) was greater than about 4%, and the amount of gallic acid was greater than about 1% after hydrolysis at 90° C. for 2 hours with methanol/HCl 1.2 M (v/v). Furthermore, the extract contained about 1.52% Vitamin C and about 66.1% polysaccharides.

Example 2

1000 kg fresh kiwi was ground and pressed and 600 kg residue was obtained as raw material. 600 g of juice was obtained. 2500 liters of 90% ethanol as solvent was added to the raw material at room temperature (20° C.) and the mixture was stirred for two hours. The extract was centrifuged. The residue was further extracted with 2500 liters 890% ethanol at room temperature (19° C.) and the mixture was stirred for one hour. The extract was centrifuged. The extracts were combined with the pressed juice and concentrated to about 650 liters at 40° C. under reduced pressure (−0.090 Mpa). 10 kg Beta-cyclodextrin were added to the concentrate with stirring until the cyclodextrin was fully dissolved. The concentrate was lyophilized to afford 61.2 Kg powder of coated kiwi extract.

The extract contained 4.8% actinidines with a biological activity of 113,000 IU/g. According to Folin-Ciocalteau assay methodology, the amount of total polyphenols was greater than about 10% (m/m), the amount of catechin (m/m) was greater than about 4%, and the amount of gallic acid was greater than about 1% after hydrolysis at 90° C. for 2 hours with methanol/HCL 1.2 M (v/v). Furthermore, the extract contained about 1.48% Vitamin C and about 65.3% polysaccharides.

Example 3

Determination of Free and Total Polyphenols

Preparation of Kiwi Samples:
Fresh kiwis (including the skin) were cleaned, mixed thoroughly, chopped into fine particles and freeze dried at −20° C.

under vacuum for 48 hours. The lyophilizate was powdered and used in the following experiments.

For the preparation of kiwi extract, fresh kiwi fruits were pressed. The residue was extracted twice with 80% ethanol (ratio residue/ethanol 80%=1/5) at room temperature for 2 hours. The ethanolic extracts were combined with the juice and evaporated to dryness under reduced pressure at 42° C. Starting from 10 kg Kiwi fruits, 0.50 kg of dried powder extract was obtained.

Extraction of Free and Total Polyphenols:

1.0 g of lyophilized kiwi fruit or kiwi extract (as produced above) was mixed with 25 ml methanol/water (1/1 v/v) and heated to 90° C. in a plastic screw-capped tube with intermittent shaking for 2 h to determine the free polyphenols present in the corresponding sample. Another 1.0 g sample of each of the lyophilized kiwi fruit and kiwi extract was heated with 25 ml of methanol/1.2 M HCl (1/1 v/v) for 2 h at 90° C. to measure the total polyphenols present in the corresponding extract [Vinson, J A, Yong H., Xuehui, S, Ligia Z, et al. J. Agric. Food Chem. (2001) 49: 5315-5321]. A minimum of 3 extractions of each material (lyophilized or extracted as prepared above) were carried out for each sample.

Determination of catechin (C), epicatechin (EC), epigallocatechin gallate (EGCG), epigallocatechin (EGC) and gallic acid (GA):

Separation of the polyphenols was carried out on a Merck HPLC gradient system with UV-detection (280 nm). A spherisorb reversed-phase C-18 (250×4.6 mm, 5 µm, Waters) column was used for separation with a linear gradient of acetonitrile and water (adjusted to pH 2.5 with concentrated HCl) at 40° C. The mobile phase gradient was adjusted from 3% acetonitrile in water at time 0 minute to 40% acetonitrile at 44 min with a flow rate of 1 ml/min. The injection volume for all samples was 10 µL. Extracts for free and total polyphenol determination were injected after filtration (0.3 µm, syringe filter) [Dawes H M, Keene J B., J. Agric. Food Chem. (1999) 47: 2398-2403].

C, EC, EGCG, EGC and GA were used as external standards. Calibration solutions were prepared by dissolution of 25 mg standard in 0.5 ml of methanol and diluted with water to 10 ml. Further dilutions were prepared by addition of water. Linear responses of the method were established between 0.6 mg/10 ml to 25.0 mg/10 ml for 3 reference compounds (C, EC and GA).

The stability of the polyphenols monomers tested (C, EC and GA) under the extraction conditions was determined. Recoveries of all 3 standards after methanolic/aqueous extraction and methanolic/acidic extraction were higher than 95% (3 concentrations, replicate extractions).

Analytical results are given as mean values (± standard deviation). Results were converted to mmol/kg dry matter.

Determination of Free and Total Polyphenols:

The sum of polyphenols monomers and oligo-/polymers was determined in the samples spectrophotometrically by the Folin-Ciocalteu assay methodology at 720 nm [Singleton V L, Orthofer R, Lamuela-Raventos, R M. Methods Enzymol. (1999) 299: 152-178]. GA was used as external standard. Results are expressed as GA-equivalents (GA-E). Control experiments showed that the recoveries of C and EC when expressed as GA-E were found to be 75%, indicating that the external calibration with GA may underestimate C and EC in samples submitted.

Figure 2:
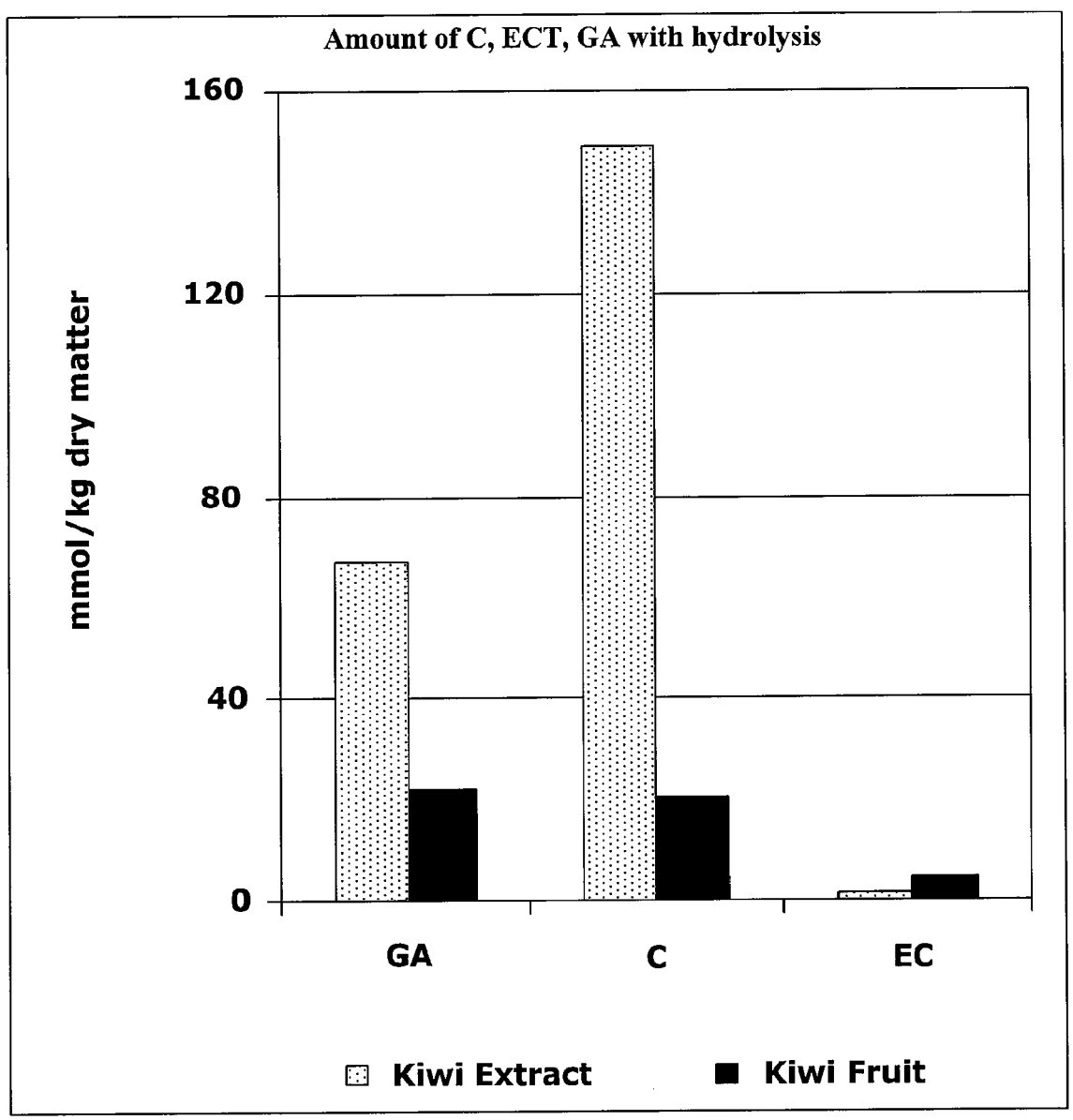

Results:

Amount of C, EC, EGCG, EGC and GA:

EGCG and EGC were not detected (<5 µg/g sample) in fresh, freeze-dried kiwi fruits (as prepared above) nor in kiwi extract after extraction with methanol/water with heating as described above. FIGS. 1 and 2 show the amount of C, ECT and GA in both samples obtained with or without hydrolysis of the polyphenols.

From the amount of C, EC and GA determined with and without hydrolysis following estimates of their relative contribution from polyphenol monomers and conjugated tannins could be derived (see Table 1).

TABLE 1

Relative contribution of C, EC and GA from polyphenol monomers and oligo-/polymers
Table 1

| Compound | Monomers (%) | | Conjugated Tannins (%) | |
| --- | --- | --- | --- | --- |
| | Kiwi Extract | Kiwi Fruit | Kiwi Extract | Kiwi Fruit |
| C | 0.8 | 9.5 | 99.2 | 90.5 |
| EC | 30.1 | 32.5 | 69.9 | 67.5 |
| GA | 2.1 | 14.4 | 97.9 | 85.6 |

Determination of Free and Total Polyphenols:

The sum of polyphenol monomers and conjugated tannins obtained by the Folin-Ciocalteu assay is shown in Table 2.

TABLE 2

Sum of polyphenols (mmol GA/kg dry matter) by Folin-Ciocalteau assay

| Free polyphenols (GA-E*) | | Total polyphenols (GA-E) | |
| --- | --- | --- | --- |
| Kiwi Extract | Kiwi Fruit | Kiwi Extract | Kiwi Fruit |
| 56.5 | 16.0 | 710 | 210 |

*Gallic Acid-Equivalents
"Kiwi fruit" is the lyophilized material described above.

The results of the methanolic/aqueous extraction indicate that the kiwi extract contains significantly less free polyphenols than the lyophilized kiwi fruit. In contrast, comparison of the methanolic/acidic extracts indicate that the kiwi extract contains more total conjugated tannins than lyophilized kiwi fruit.

A substantial difference in the content of GA and C was observed in the kiwi extract after acidic extraction as compared to aqueous extraction. The proportional increases observed were by factors of 47, 120 and 2.3 for GA, C and EC, respectively. The proportional increases found for lyophilized kiwi fruit were by factors of 6, 10 and 2.0, respectively. Most interestingly, the increase in GA and C is much higher in the kiwi extract as compared to the lyophilized kiwi fruit, whereas the EC increase was comparable. These findings indicate that, firstly, the kiwi extract is enriched in conjugated tannins and, secondly, that EC does not appear to contribute to the condensed tannin content in a major amount.

It was also found that more than 97% of the polyphenols in the kiwi extract were comprised of conjugated tannins. In lyophilized kiwi fruit, a significantly lower proportion of about 73% of the polyphenols belong to conjugated tannins.

In kiwi extract and lyophilized kiwi fruit, about 30% and 23%, respectively, of the free polyphenols, determined with the Folin-Ciocalteu-assay, are represented by GA, C and EC.

In kiwi extract and lyophilized kiwi fruit, about 45% and 30%, respectively, of total polyphenols are represented by GA, C and EC.

Example 4

Test of Lipase Inhibition

Lipase Inhibition Test

Chemicals:

Reference standards and organic solvents (ACS or HPLC grade) were obtained from Sigma Aldrich (Vienna, Austria). Standard laboratory chemicals were p.a grade. The lipase test kit was obtained from Trinity Biotech (Jamestown, N.Y., USA, Cat No.: 805).

Kiwi Samples:

Fresh Kiwis (commonly consumed cultivars from New Zealand) were cleaned, mixed thoroughly and lyophilized. The lyophilisate was powdered and used as the sample denoted as kiwi powder. Starting from 10 kg kiwi fruit, 1.20 kg of dried kiwi lyophilisate was obtained.

Kiwi extract was prepared from fresh kiwi fruit which were pressed to yield kiwi juice. The pressing cake was extracted twice with 80% ethanol (ratio residue/ethanol=1/5). The ethanolic extracts were combined with the juice and evaporated to dryness under reduced pressure at 45° C. On average 10 kg Kiwi fruits yield about 0.50 kg of dried powder kiwi extract.

Sample Preparation:

0.5-4.0 g kiwi lyophilisate or kiwi extract were suspended in 100 ml acetone/water=6/4 and stirred for 12 hours at room temperature for extraction of polyphenols. Following centrifugation at 5.000 rpm for 10 minutes, the clear supernatant was evaporated to dryness under reduced pressure at 45° C. The dry residue was submitted to the following investigations.

Extraction of Free and Hydrolysis of Conjugated Polyphenols:

Dry residue samples prepared from 1 g samples of kiwi lyophilisate or kiwi extract were dissolved in 100 ml $CH_3OH/H_2O$ (1/1 v/v) and heated to 90° C. for 2 h in a plastic screw-capped tube with intermittent shaking for 2 h to extract "free polyphenols" present in the samples. Another series of equally prepared samples were dissolved in 100 ml of $CH_3OH/HCl$ 1.2 M (1/1 v/v) and heated to 90° C. for 2 h to yield the "total polyphenols" by hydrolysis of the conjugated polyphenols present in the samples. Prior to the determination of the polyphenols, the samples were centrifuged (5.000 rpm for 5 min.) and further cleared by filtration (syringe filter 2 µM). A minimum of 3 replicates were carried out for each sample.

Determination of Polyphenols:

Polyphenols were determined spectrophotometrically by the Folin-Ciocalteu assay methodology at 720 nm. Gallic Acid (GA) was used for external standardization. Results are expressed as GA-equivalents (GA-E). Control experiments with solutions containing catechin, epicatechin, tannic acid and coumaric acid showed that recoveries of >80% were obtained when expressed as GA-E (data not shown). The difference between the concentrations obtained for "free polyphenols" and "total polyphenols" was attributed to the fraction of "conjugated polyphenols".

Analytical results are given as mean values (n=3). Results were converted to µmol GA-E/mg dry matter.

Lipase Activity Test (Lipase Activity Test)

Dry residue samples prepared from 0.5, 1.0, 1.5, 4.0 g starting material (kiwi lyophilisate or kiwi extract) were dissolved in 100 ml $CH_3OH/H_2O$ (1/1 v/v), centrifuged (5.000 rpm for 5 min.) and cleared by filtration (syringe filter 20 µM). These samples represent concentrations of 5, 10, 15 and 40 mg kiwi lyophilisate or kiwi extract/ml solvent. Control experiments were performed using the solvent.

Another series of samples prepared from 4.0 g starting material was heated in 100 ml of $CH_3OH/HCl$ 1.2 M (1/1 v/v). These samples were then neutralized to pH 7.0 (NaOH) and evaporated to dryness under reduced pressure at 45° C. The residue was dissolved in 100 ml $CH_3OH/H_2O$ (1/1 v/v), centrifuged (5.000 rpm for 5 min.) and cleared by filtration (syringe filter 2 µM).

Lipase activity was determined using a commercially available test kit. In short, aliquots of LPS standard, solvent or samples were added to 500 µl of substrate solution, mixed gently and incubated for 5 min at 37° C. After addition of an activator reagent the change in the absorbance rate was followed at 550 nm for 10 minutes. The rate of activity is given as % of the activity of Lipase PS (labeled with 327 IU/L) obtained from control samples.

Results:

After extraction of 0.5-4.0 g sample with acetone/water the dry mass obtained from kiwi lyophilisate and kiwi extract was on average 25±3% and 48±2%, respectively. The distribution and content of free, conjugated and total polyphenols in these samples is shown in Table 1. Kiwi lyophilisate and kiwi extract contain 26.5% and 7.9%, respectively, of total polyphenols as free polyphenols. The corresponding figure for conjugated polyphenols is 73.5% and 92.1%, respectively.

TABLE 1

Free and Total polyphenols (µmol GA-E/mg dry mass)

|  | Kiwi Lyophilisate | Kiwi Extract |
|---|---|---|
| Free polyphenols (GA-E*) | 0.076 | 0.057 |
| Conjugated polyphenols (GA-E) | 0.21 | 0.653 |
| Total polyphenols (GA-E) | 0.286 | 0.710 |

*Gallic Acid-Equivalents

Figure 3:
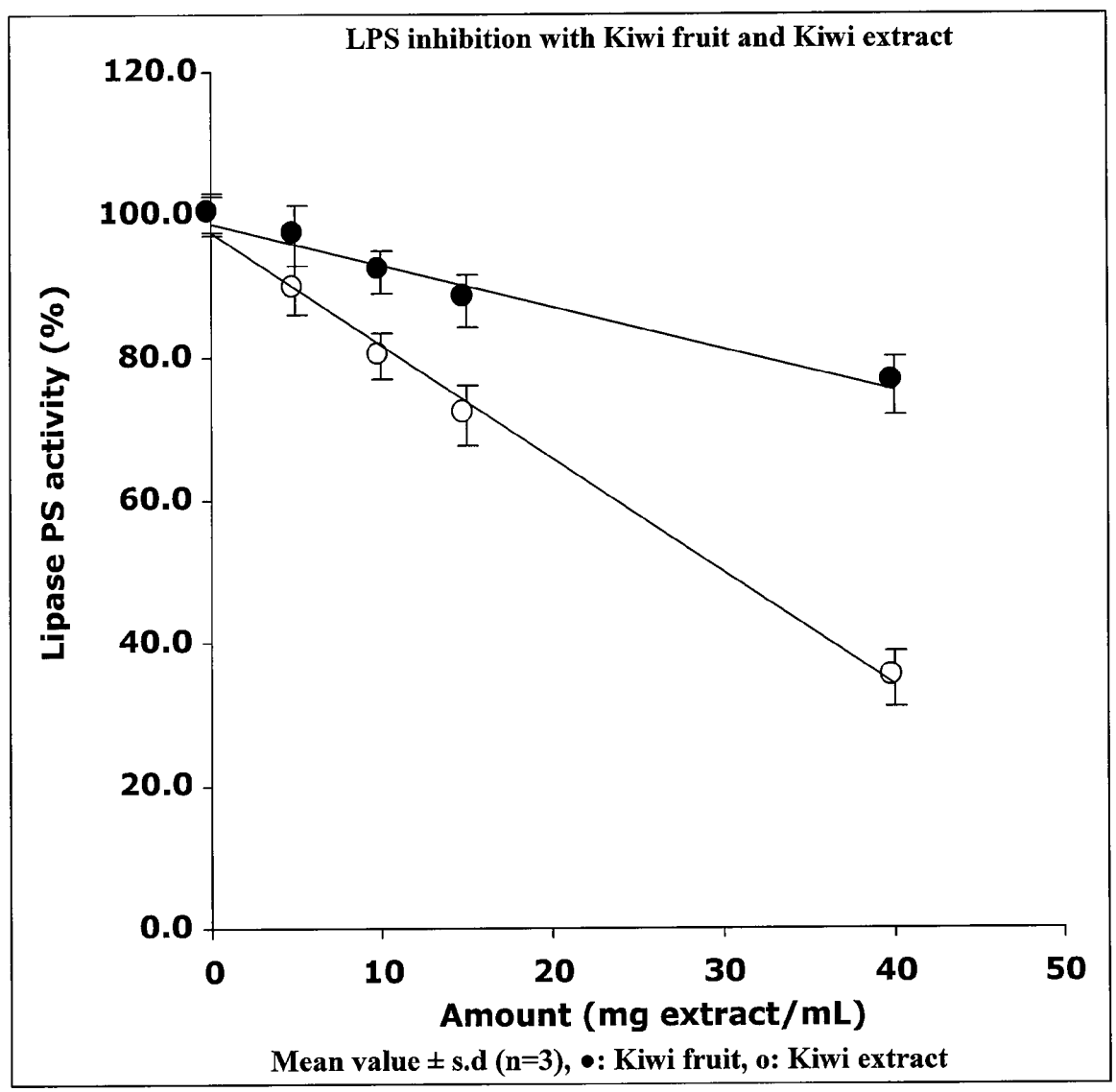
FIG. 3 shows the results of LPS inhibition tests with kiwi fruit and kiwi extract.

Lipase Activity:

The influence on the LPS activity in presence of kiwi lyophilisate and kiwi extract in different concentrations are shown in FIG. 3. On basis of the concentration of the staring material kiwi extract was found to inhibit LPS considerably stronger than the kiwi lyophilisate.

Figure 4:
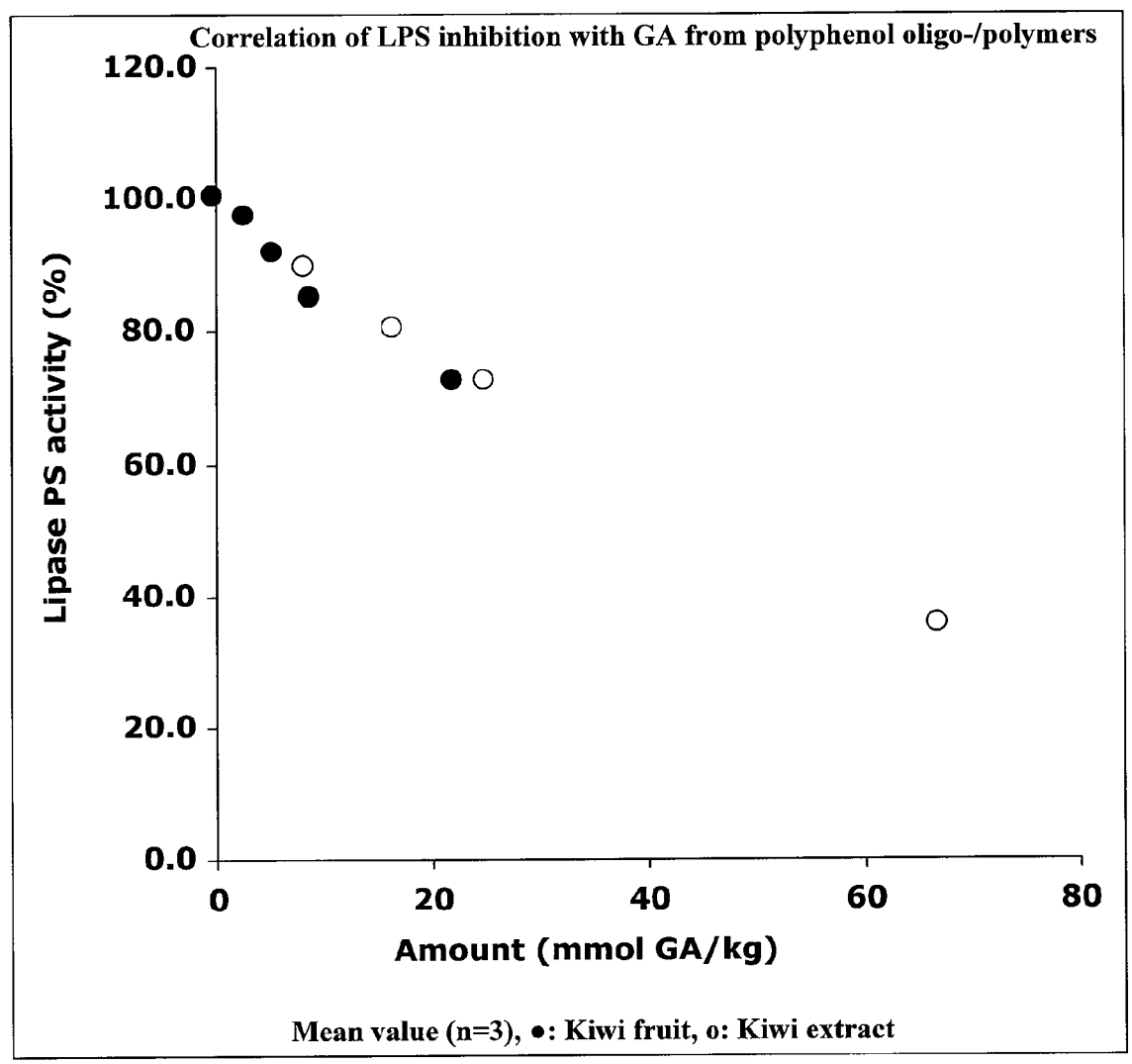
FIG. 4 shows the correlation of LPS inhibition with GA representative of the polyphenol oligo-/polymers.

As seen in Table 1, kiwi extract contains considerably more conjugated polyphenols than the kiwi lyophilisate. To correct for these differences the concentrations given were converted to GA-E attributable to the fraction of conjugated polyphenols (FIG. 4). This conversion yields a dose-proportional increase of the LPS inhibition, almost independently of the sample type (kiwi lyophilisate or kiwi extract).

To further explore the role of the conjugated polyphenols, the activity of the LPS was tested in presence of the kiwi lyophilisate and kiwi extract (each at a concentration of 40 mg/ml) after acidic hydrolysis. The results obtained with these samples being essentially free of conjugated polyphenols were compared to the results obtained with equally concentrated samples with an intact fraction of conjugated polyphenols (Table 2). As seen, the LPS inhibition is almost completely lost after hydrolysis of the polyphenols and loss of the fraction of conjugated polyphenols.

TABLE 2

LPS activity with/without acidic hydrolysis (%)

| | % LPS-activity | |
|---|---|---|
| | Kiwi lyophilisate | Kiwi Extract |
| Non-hydrolyzed polyphenols | 35 | 72 |
| Hydrolyzed polyphenols | 93 | 95 |

Figure 5:
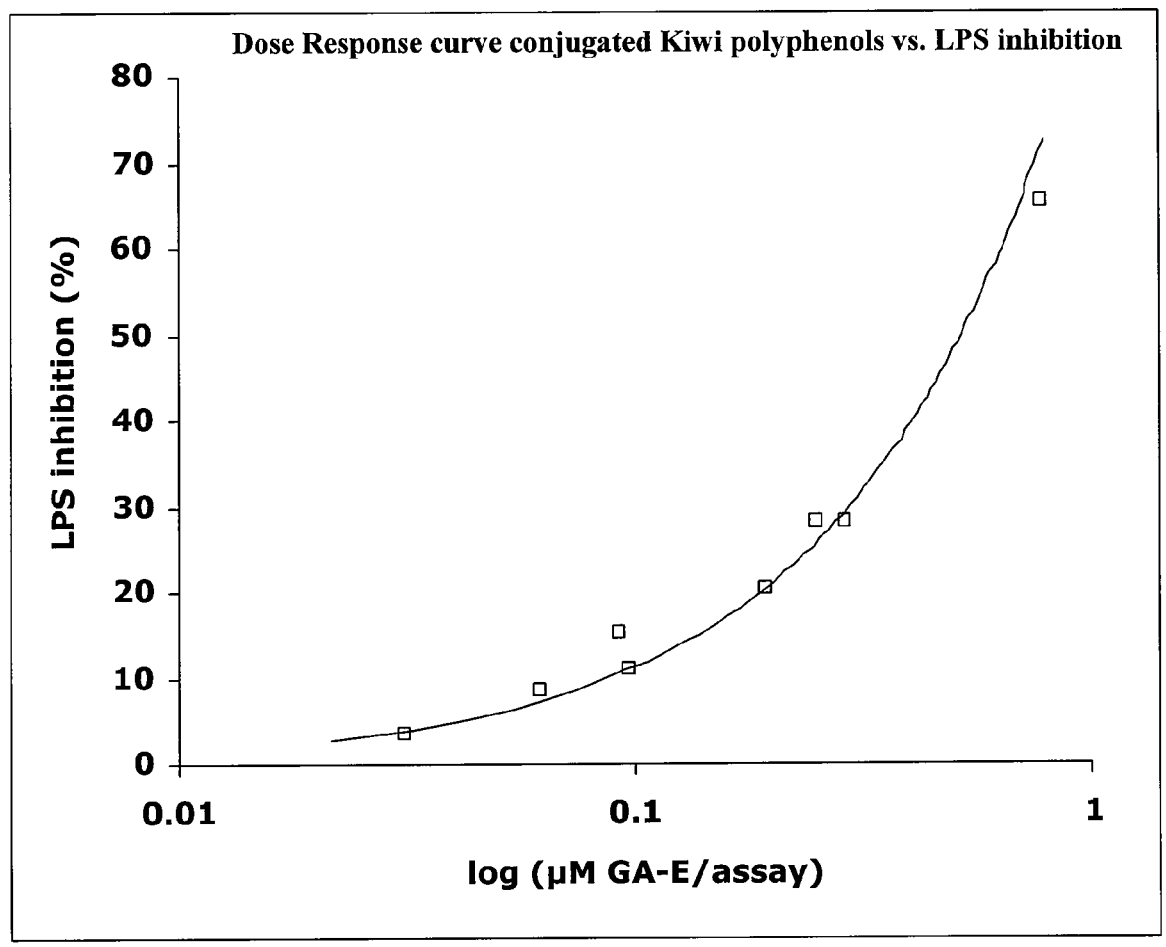
FIG. 5 provides a dose Response curve conjugated kiwi polyphenols vs. LPS inhibition.

As presented in FIG. 5, a smooth dose-response curve was derived from the pooled results of the LPS inhibition versus the fraction of conjugated polyphenols expressed as GA-E.

Discussion:

The results of the determination of polyphenols indicate that kiwi extract and the kiwi lyophilisate contain similar amounts of free polyphenols indicating that the extraction procedure preserves this fraction of polyphenols. The absolute amount and the proportions of free and total polyphenols observed in kiwi lyophilisate is in the range of published results. In kiwi lyophilisate about 70% of the total polyphenols are present as conjugated polyphenols. With more than 92% of the total polyphenols, a significantly higher proportion of conjugated polyphenols were observed in kiwi extract. Apart from the proportion also the absolute amounts of conjugated polyphenols are increased in kiwi extract even when corrected for the different extraction yield. It is therefore concluded that the extraction procedure is efficiently concentrating conjugated polyphenols from kiwi fruit.

The high proportion of conjugated polyphenols observed is especially important for this study as free polyphenols were shown to be weak inhibitors of the LPS with $IC_{50}$-values of >20 μM for catechin, epicatechin and gallic acid.

In the study at hand kiwi lyophilisate and kiwi extract were shown to inhibit LPS. Based on the concentration (mg dry mass/ml), kiwi extract was much more potent that the kiwi lyophilisate. When correcting the concentration for the GA-E of the conjugated polyphenols contained in the corresponding samples, a dose-proportional increase of the LPS inhibition was found. Of interest, the dose-proportionality obtained was independent from the source of the conjugated polyphenols fraction (the kiwi lyophilisate and kiwi extract). This helps maintain that the kiwi extract contains a similar, if not the same, composition of conjugated polyphenols but in a higher concentration. When considering the similar amount of free polyphenols present in the kiwi lyophilisate and kiwi extract, the LPS inhibiting properties can be clearly attributed to the fraction of conjugated polyphenols.

To further support these results hydrolyzed kiwi samples which are essentially free from conjugated polyphenols were tested for inhibition of LPS. The results of these tests showed clearly that the LPS inhibition properties are almost completely lost when no conjugated polyphenols are present in the samples. These results point again to published findings that soluble polyphenols are only weak inhibitors of the LPS.

Example 5

Inhibition of Chicken Liver Fatty Acid Synthase by Kiwi Extract

Materials and Methods:

Chemicals:

$NaH_2PO_4$-Merck A168646, Glycerol-Sigma G5516, NaOH-Aldrich 22,146-5, Sephadex G-50-Sigma G-50-80, Ethylendiaminetetraacetic acid EDTA-Sigma E9884, Dithithreiol DTT-Sigma D-9779, polyethylene glycol 6.000 Fluka-81255, DEAE-cellulose-Fluka 30477, Nicotinamide adenine di-nucleotide-phosphate $NADPH_2$-SIGMA N-7505, malonyl-CoA-Sigma M-4263, acetyl-CoA-Sigma A-2056, Total Protein Kit-SIGMA TP0200, Bovine Albumin-Fluka 05473.

Extraction of FAS from Chicken Liver:

Liver from young chicken (0.5 kg BW (body weight)) was excised immediately after the animals have been sacrificed and stored on ice until further processing. 10 g of minced liver were homogenized in 100 ml ice-cold buffer (0.1 M $NaH_2PO_4$-buffer with 20% glycerol, pH adjusted to 7.5 with NaOH) using a mechanical homogenizer. The homogenate was centrifuged at 4° C. for 15 min. at 30.000 g.

The resulting supernatant (liberated from the fat layer) was immediately further processed by gel filtration over Sephadex G-50. The gel-filtration was performed using 100 ml cartridges from Pharmacia filled with Sephadex G-50 suspended in water. The flow rate was set to approximately 4 ml/min. The elution was followed by UV-detection set to 214 nm. The mobile phase consisted of 0.1 M $NaH_2PO_4$-buffer, 45 mM glycerol, 1 mM EDTA, 1 mM DTT, pH adjusted to 7.5 with NaOH. The first peak corresponding to the protein fraction was collected and pooled (40 ml volume).

The protein fraction was made up to 5% (m/v) polyethyleneglycol and stirred for 30 min. at 4° C. The precipitate was separated by centrifugation (9.000 g, 30 min. 4° C.) and the supernatant was brought to 12% concentration with polyethyleneglycol. The resulting precipitate was collected by centrifugation (9.000 g, 30 min. 4° C.) and used for further processing.

The pellet was carefully washed and then dissolved in 5 ml 0.1 M $NaH_2PO_4$-buffer, 45 mM glycerol, 1 mM EDTA, 1 mM DTT, pH adjusted to 7.5 with NaOH. This solution was filtered if necessary and stored at −20° C. without loss of activity for 4 weeks.

As last purification step performed immediately prior to the assay, the resulting solution was purified by ion-exchange chromatography with DEAE-cellulose. In this case glass-pipettes were filled with a 1 ml volume of DEAE-cellulose and equilibrated with 0.1 M $NaH_2PO_4$-buffer, 45 mM glycerol, 1 mM EDTA, 1 mM DTT, pH adjusted to 7.5 with NaOH. 0.5 ml of the protein solution was loaded onto the column and eluted by step-wise addition of 0.5 ml portions of the same buffer. The fractions eluting between 1.5-2.5 ml were collected and used for the FAS-assay.

FAS Test-Assay (FAS Test):

150 μl of the purified extract were mixed with 100 μl $NADPH_2$/Ac—CoA (2.5/0.8 mg/2 ml water corresponding to a final concentration of 150 and 50 μM, respectively). A solution of kiwi extract, as prepared below, was added in volumes of up to 250 μL.

The test assay was then filled up to 1 ml with 0.1 M $NaH_2PO_4$-buffer, 45 mM glycerol, 1 mM EDTA, 1 mM DTT, pH adjusted to 7.5 with NaOH. After a 30 min. pre-incubation period at 25° C., 100 μl malonyl-CoA (1 mg/2 ml water corresponding to 55 μM) were added as a reaction starter. The reaction was monitored with an UV/VIS spectrometer (Jasco V-530) set to 340 nm against air at 30° C. The activity of the enzyme was calculated from the decrease of absorption which is due to consumption of $NADPH_2$. The measurement time was set to 15 min.

Variations to the general procedure are further explained in the result section.

Preparation and Evaluation of Kiwi Extract Samples:

Fresh Kiwi fruits were pressed. The residue of pressing was extracted twice with 80% ethanol (ratio residue/80% ethanol=1/5). The ethanolic extracts were combined with the juice and evaporated to dryness under reduced pressure at 42° C. Starting from 1.000 kg Kiwi fruits, 50 kg of dried powder extract were obtained.

Kiwi extract was in dissolved ethanol and diluted with test-assay buffer to a final concentration of 2 mg/ml.

The extraction of free and total polyphenols was carried out according to a known procedure. In brief, a weighed portion (1.0 g) of kiwi extract was mixed with 25 ml methanol/water (1/1 v/v) and heated to 90° C. in a plastic screw-capped tube with intermittent shaking for 2 h to determine the free polyphenols present in the corresponding extract. Another weighed sample was heated with 25 ml of methanol/1.2 M HCl (1/1 v/v) for 2 h at 90° C. to measure the total polyphenols present in the corresponding extract. A minimum of 3 extractions were carried out.

Separation of polyphenols was carried out on a Merck HPLC gradient system and UV-detection (280 nm). A Waters spherisorb reversed-phase C-18 (250×4.6 mm, 5 μm) column was used for separation with a linear gradient of acetonitrile and water (adjusted to pH 2.5 with concentrated HCl) at 40° C. The mobile phase gradient was adjusted from 3% acetonitrile in water (pH=2.5) at time 0 min to 40% acetonitrile in water (pH=2.5) at 44 min with a flow rate of 1 ml/min. The injection volume for all samples was 10 μL. Extracts for free and total polyphenol determination were injected after filtration (0.3 μm, syringe filter) and 1:4 (v/v) dilution with water.

Gallic Acid, Catechin and Epicatechin were used as external standards. Calibration solutions were prepared by dissolution of 25 mg standard in 0.5 ml of methanol and dilution with water to 10 ml. Further dilutions were prepared by addition of water. The linear relationship of the method was established between 0.6 mg/10 ml to 24.0 mg/10 ml for all 3 reference compounds.

The stability of Gallic Acid, Catechin and Epicatechin under the extraction conditions was determined. Recoveries of all 3 standards after methanolic/aqueous extraction and methanolic/acidic extraction were higher than 95% (3 concentrations, replicate extractions).

Protein Determination:

Protein was determined according to a modified Micro-Lowry method (Total Protein Kit, Micro Lowry, Onishi & Barr Modification) according to the manual. As calibration range 0.15-1.0 mg protein/ml was used. The method was calibrated with bovine albumin.

Calculations:

The activity of the FAS was calculated from the consumption of NADPH expressed as $\mu M \times L^{-1} \times min^{-1}$ using the absorption data obtained and a molar extinction coefficient of 6.3.

Results

Figure 6:
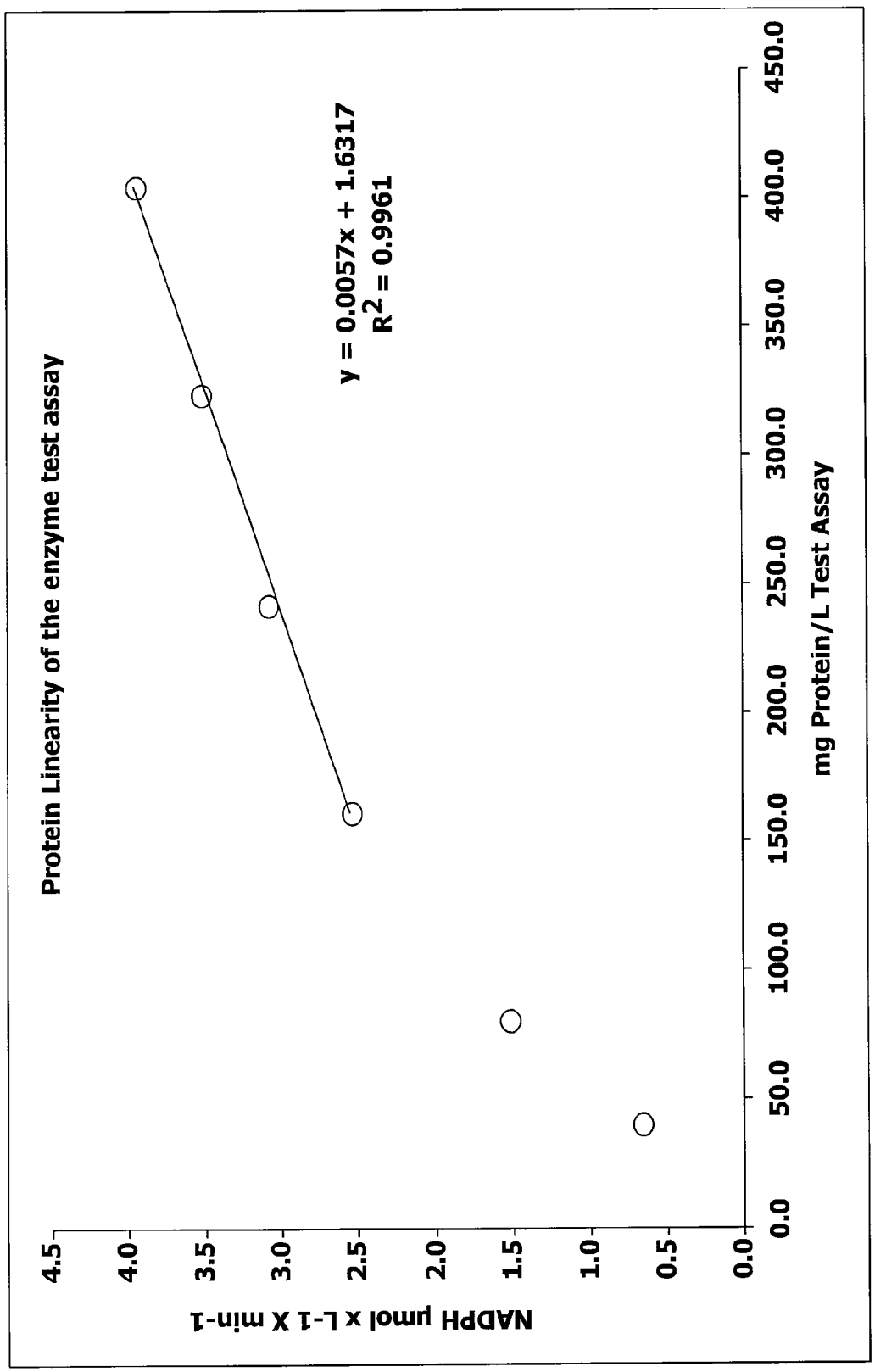
FIG. 6 shows the protein linearity of the FAS-enzyme test assay.

Enzyme Characteristics:

The protein linear relationship was estimated by addition of various volumes of the purified enzyme extract to the test assay system, which contained 1.8 g protein/L extract. The resulting curve is presented in FIG. 6, where each point represents the average of 3 experiments. As seen, the linear part of the test assay ranged from 175 mg to 450 mg protein/L test assay with a coefficient of correlation of 0.9961. With higher concentrations, a ceiling effect with respect to the activity was observed. From these investigations a protein content of 270 mg protein/L corresponding to 150 μL purified extract was chosen.

Figure 7:
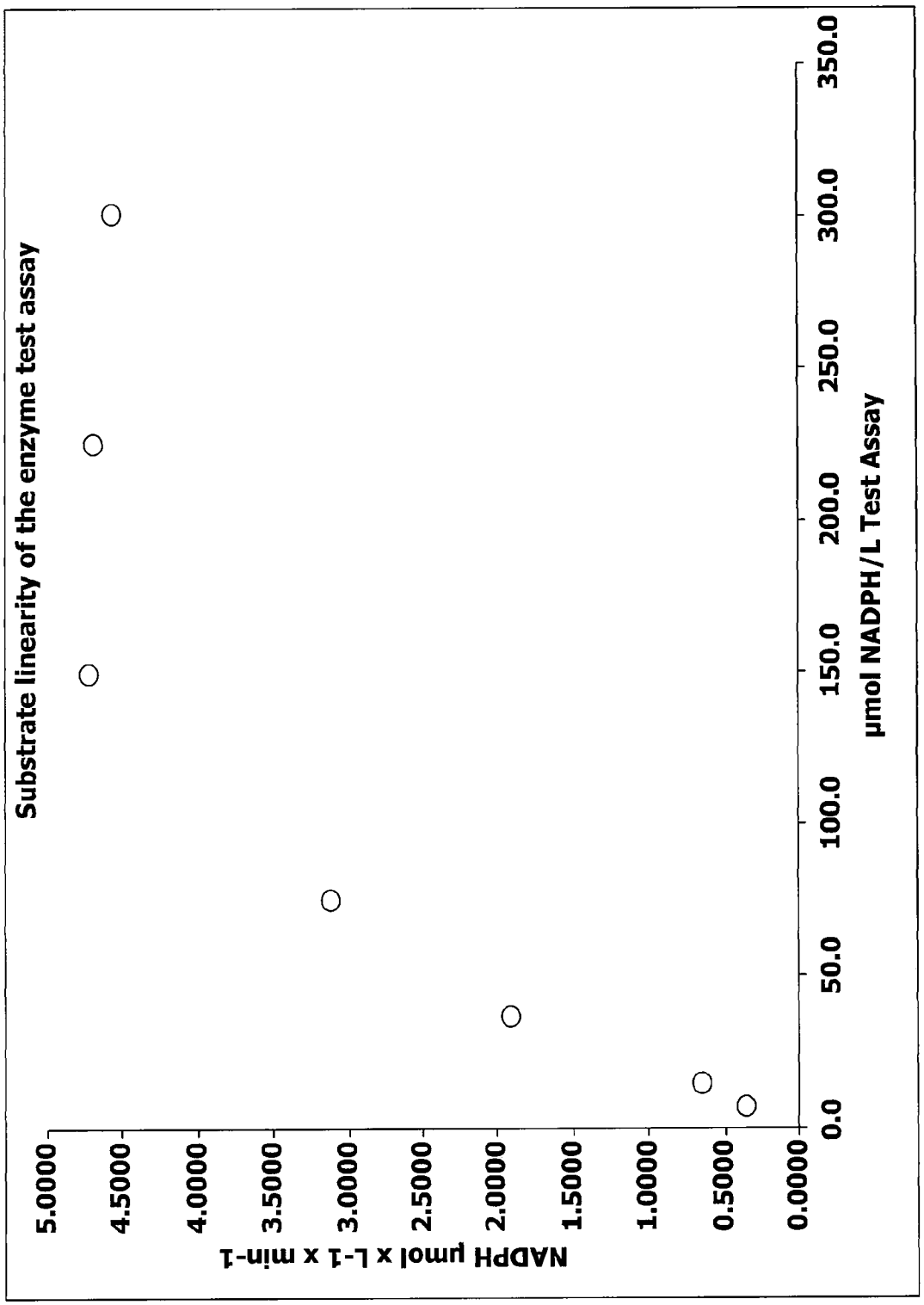
FIG. 7 shows the substrate linearity of the FAS-enzyme test assay.

For the determination of the substrate linearity NADPH was added in varying amounts in a range of 5-350 μM NADPH/L test assay. Malonyl-CoA was added in excess and was, therefore, not further investigated. The results are presented in FIG. 7, where each point represents the average of 3 experiments. As seen there, the maximum activity was achieved at 150 μM $NADPH_2$/L test assay, hence this concentration was chosen for the test-assay.

The time of incubation was investigated by measuring the change of absorption at 340 nm over 60 min. It could be shown that the activity of the enzyme disappeared after 15 min. of measurement, corresponding to no further increase of the absorption. Hence, the incubation time was set to 15 minutes.

The incubation temperature was set to 30° C. as comparative experiments at 20, 25 and at 35° C. yielded only negligible in FAS activity. It was concluded that the temperature has no major influence on the test system.

Further on it was shown that potential solvents used for the dissolution of the extracts (DMSO, 10% ethanol) had no influence on the enzyme activity when compared to control experiments (Data not shown).

Figure 8:
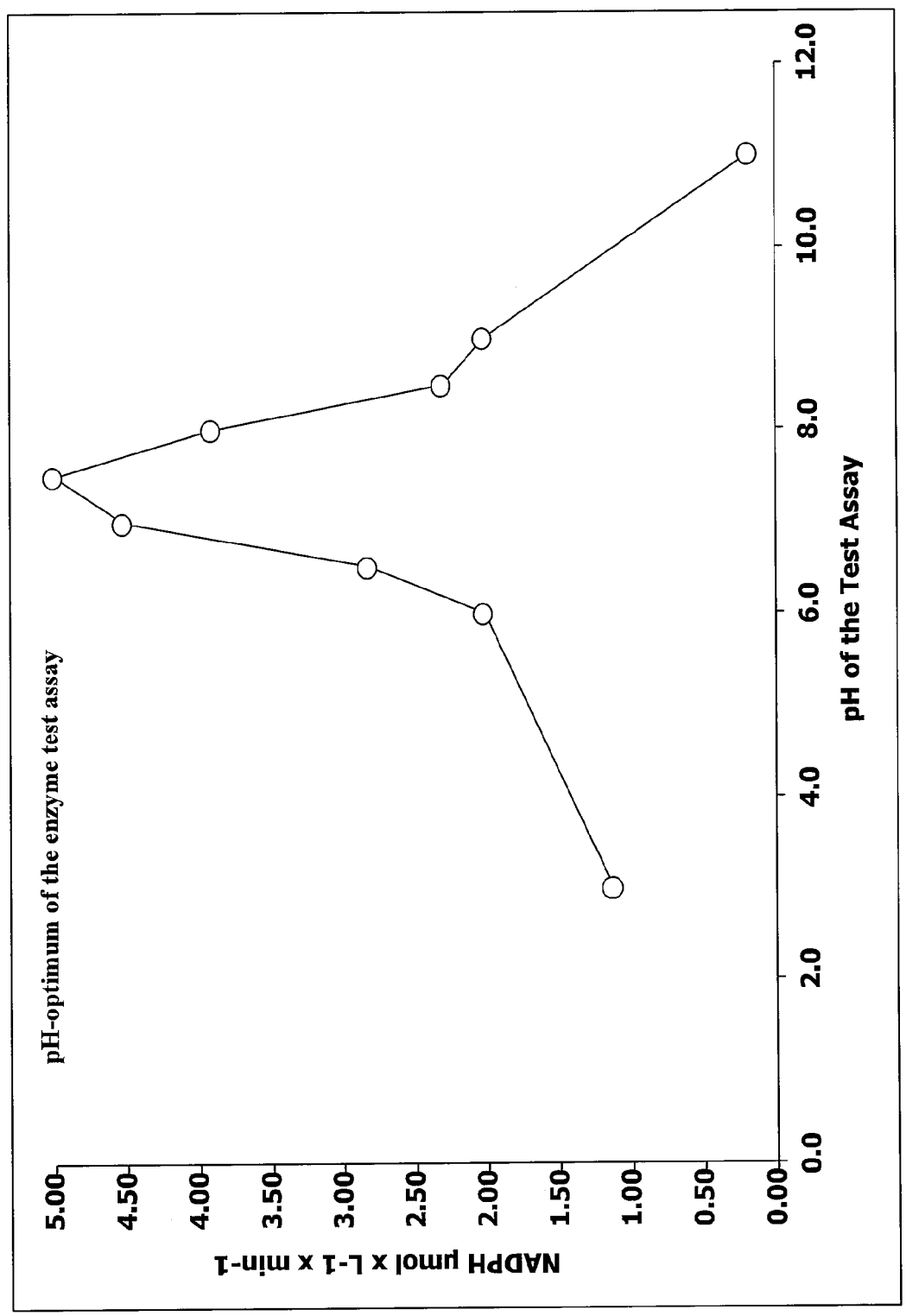
FIG. 8 shows the pH-optimum of the FAS-enzyme test assay.

For the determination of the pH-optimum the test buffer added was adjusted to pH-values between 3 and 11. The results are presented in FIG. 8 where each point represents the average of 3 experiments. As seen, the pH-optimum was found to be around 7.5. Therefore, a pH of 7.5 was chosen for further investigations.

The optimized test-assay for the FAS was used to perform inhibition experiments with Kiwi extract.

Figure 9:
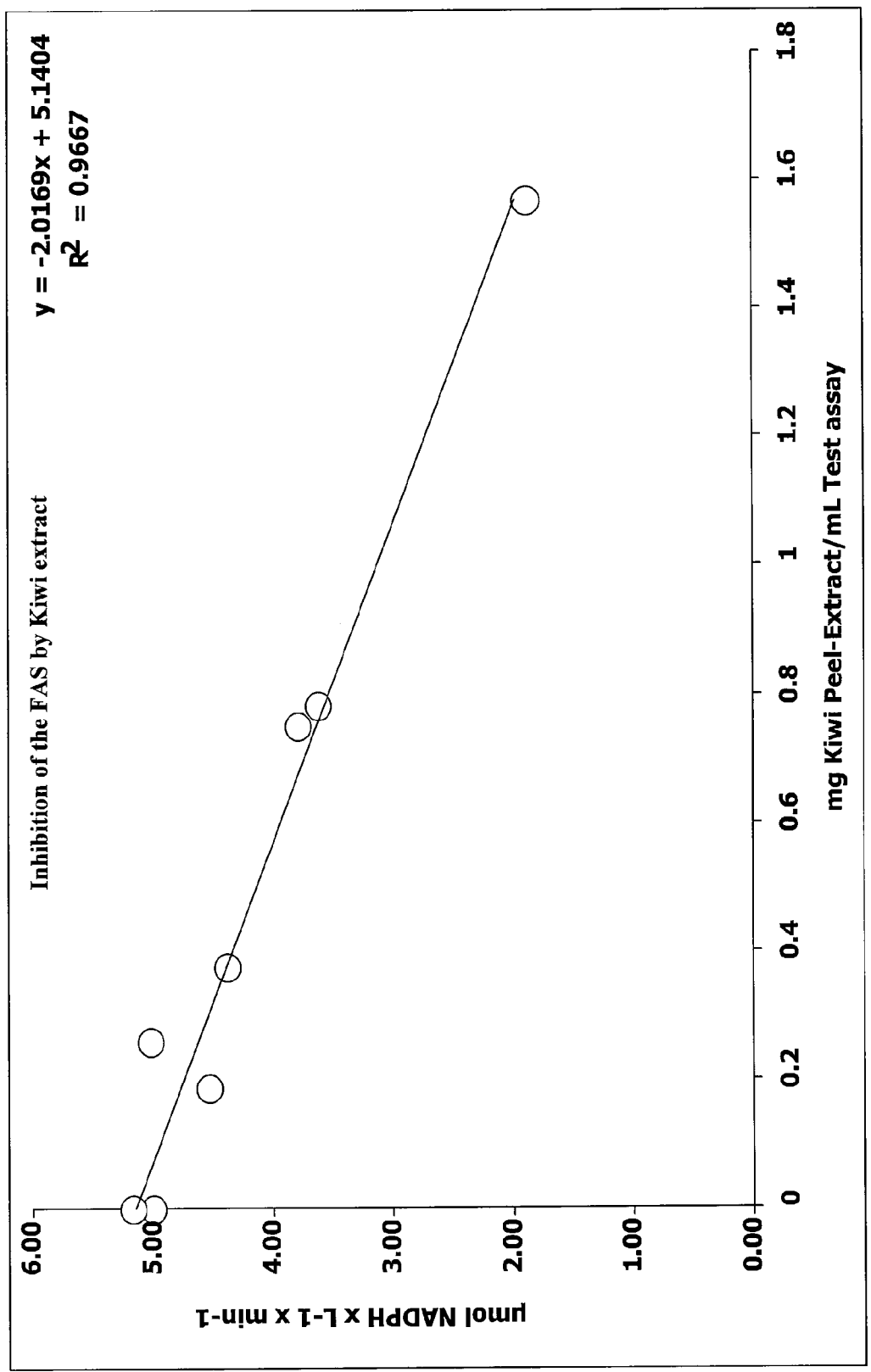
FIG. 9 shows the inhibition of FAS by kiwi extract.

Inhibition Experiments:

The kiwi extract was dissolved in ethanol and diluted with test-assay buffer to a final concentration of. After filtration, varying amounts of the kiwi extract solution (2 mg Kiwi extract/ml were added to the FAS test-assay. The results obtained are shown in FIG. 9 where each point represents the average of 3 experiments. As seen, the extract was shown to inhibit the FAS in a strong dose-dependent manner. At the highest concentration tested an inhibition of around 60% was seen.

Discussion

The FAS was extracted and partly purified from chicken liver. The properties of the FAS resemble very much the properties of the human FAS. The purification procedure and the test assay were thoroughly investigated. It could be convincingly demonstrated that the assay developed works satisfactory to investigate potential inhibitors of the FAS.

Inhibition experiments yielded substantial inhibition of the FAS by the kiwi extract. The kiwi extract at hand yielded an FAS activity inhibition of up to around 60% at concentrations of 1.8 mg extract/ml test assay. These inhibitory concentrations are rather high, but were obtained with crude extracts. In case that the constituents of these extracts are elucidated qualitatively and quantitatively it might well be expected to find one or more lead compounds responsible for the activity. Based on current knowledge the most likely candidates with substantial activity are flavonoids or polyphenols.

Summarizing it could be stated that Kiwi extract seem to possess substantial FAS inhibitory constituents and may, therefore, be used for the inhibition of the FAS also in humans in conditions were high FAS activity is correlated with hypertriglyceridema.

Although the present invention has been described with reference to preferred embodiments, persons skilled in the art will recognize that changes may be made in form and detail without departing from the spirit and scope of the invention.

All references cited throughout the specification, including those in the background, are incorporated herein in their entirety.

Properties of Kiwi Extracts—Summary

Chemistry/Analytical Data:

The kiwi extracts discussed herein contain more than 10% (m/m) condensed polyphenols.

1 g kiwi extract contains about 609 μmol gallic acid equivalents of phenolic compounds.

1 g kiwi extract contains about 398 μmol catechin equivalents of phenolic compounds.

The condensed kiwi extract polyphenols are composed of gallic acid-, caffeic acid- and catechin-related monomers in a statistical ratio of about 10:10:1, respectively.

The average molecular weight of the condensed kiwi extract polyphenols is about 3000, suggesting a degree of polymerization of about 20.

Biological Effects:

Efficacy

Kiwi extract inhibits Fatty Acid Synthase (type I) substantially.

In the FAS test as described above, an equivalent of 0.8 μmol GA-E in kiwi extract yield a 50% inhibition of the Fatty Acid Synthase (type I) activity.

Kiwi extract inhibits Human Lipase PS substantially.

In the Lipase Activity Test (as described above) an equivalent of 18 μmol GA-E in kiwi extract yield a 50% inhibition of the Human Lipase PS activity.

Purified, condensed kiwi extract polyphenols inhibit Human Lipase PS substantially.

More than 90% of the total Human Lipase PS inhibition activity resides in the condensed kiwi extract polyphenols. It has been found that the inhibitory activity is almost completely lost when the condensed kiwi extract polyphenols are hydrolyzed.

Based on the in-vitro investigations performed, an orally effective dose is between about 0.5-1.0 g. kiwi extract for a substantial Human Lipase Inhibition is estimated.

Safety

In biologically relevant amounts, purified condensed kiwi extract polyphenols do not precipitate bovine serum albumin.

Chemical Properties of Kiwi Extract:

Polyphenolic Composition of Kiwi Extract

The content of polyphenols in kiwi extract is allocated to following classes:

(a) Soluble or free polyphenols: Refers to groups of simple phenolic compounds as exemplified by gallic acid related, caffeic acid related and catechin related "soluble phenols". Chemically they dissolve in methanol/water.

(b) Condensed polyphenols: Refers to higher molecular weight phenols composed of monomers from various phenolic compound groups. The monomeric building blocks are derived from gallic acid related, caffeic acid related or catechin related compounds.

Quantification of polyphenols is standardized against gallic acid. Hence, the content of polyphenols can be given as "gallic acid equivalents" (GA-E). The concept of GA-E is important, as it makes it possible to compare Kiwi extract with published results. Basically, GA-Es are equal to "content of polyphenols expressed as gallic acid".

1 g kiwi extract equals 609 umol GA-E.

Based on the test results for the polyphenols in kiwi extract following composition was observed:

| | Polyphenols expressed as pMol Gallic Acid equivalents/g dry mass | | |
|---|---|---|---|
| | Soluble fraction | Condensed fraction | Total |
| Kiwi extract | 12 | 597 | 609 |
| Kiwi (average)[1)] | 48 | 75 | 123 |
| Apple (average)[1)] | 123 | 67 | 160 |
| Plum (average)[1)] | 157 | 23 | 180 |

[1)]Literature values

On a mass/mass basis the content of polyphenols is given as:

0.22% (m/m) soluble polyphenols, equivalent to about 2.2 g/kg kiwi extract 11.25% (m/m) condensed polyphenols equivalent to about 112.5 g/kg kiwi extract 11.45% (m/m) total polyphenols equivalent to about 114.5 g/kg kiwi extract Characterization of the Condensed Kiwi Extract Polyphenols Condensed polyphenols are defined as oligo-/polymeric compounds composed of monomeric building blocks derived from different phenolic classes.

The condensed kiwi extract polyphenols were isolated. Using well established procedures, 11.25% (m/m) condensed kiwi extract polyphenols were obtained in solid form.

The monomeric building blocks of the condensed polyphenols were characterized. 3 typical lead compound classes of monomeric building blocks were observed and tested by HPLC. The following results were obtained:

TABLE

| Monomeric building blocks of condensed Kiwi extract polyphenols | | | |
|---|---|---|---|
| Monomeric building blocks of condensed Kiwi Extract polyphenols [% m/m] | | | |
| | Gallic Acid related | Caffeic Acid related | Catechin related |
| Kiwi extract | 4.34 | 4.45 | 0.43 |

Selected chemical structures of monomeric building blocks of condensed kiwi extract polyphenols:

Selected chemical structures of monomeric building blocks of condensed kiwi extract polyphenols:

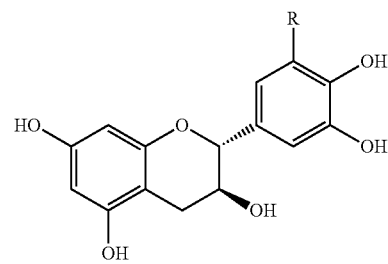

R = H: (+)-catechin
R = OH: (+)-gallocatechin

-continued

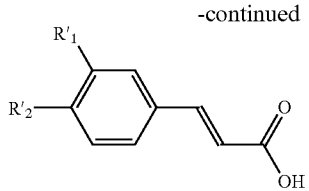

R'1 = R'2 = OH: Caffeic Acid
R'1 = OH, R'2 = H: Coumaric Acid
R'1 = OCH₃, R'2 = OH: Ferulic Acid

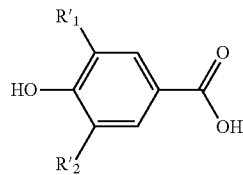

Figure 10:
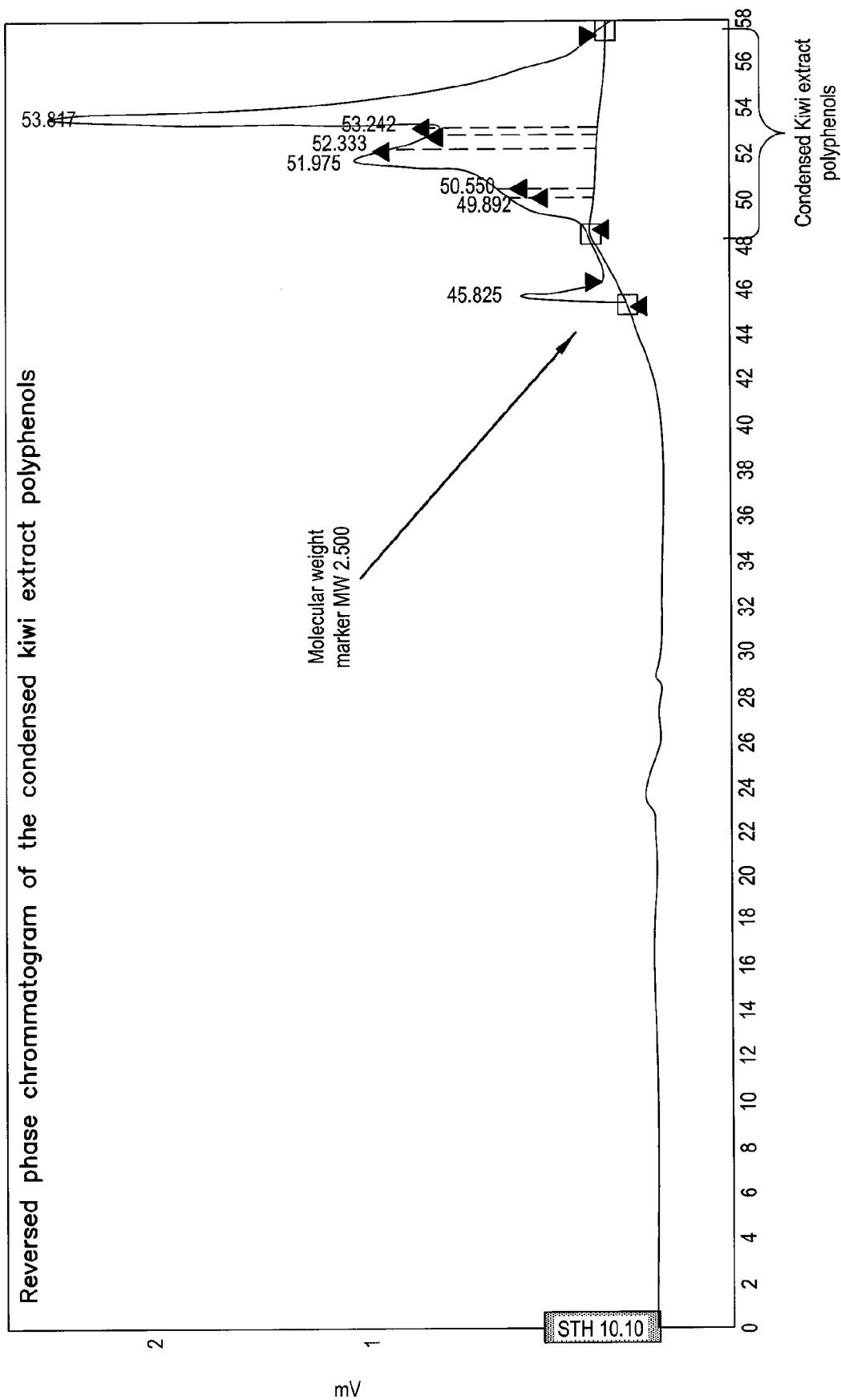
FIG. 10 is a reversed phase chromatogram of the condensed Kiwi extract polyphenols.
Figure 11:
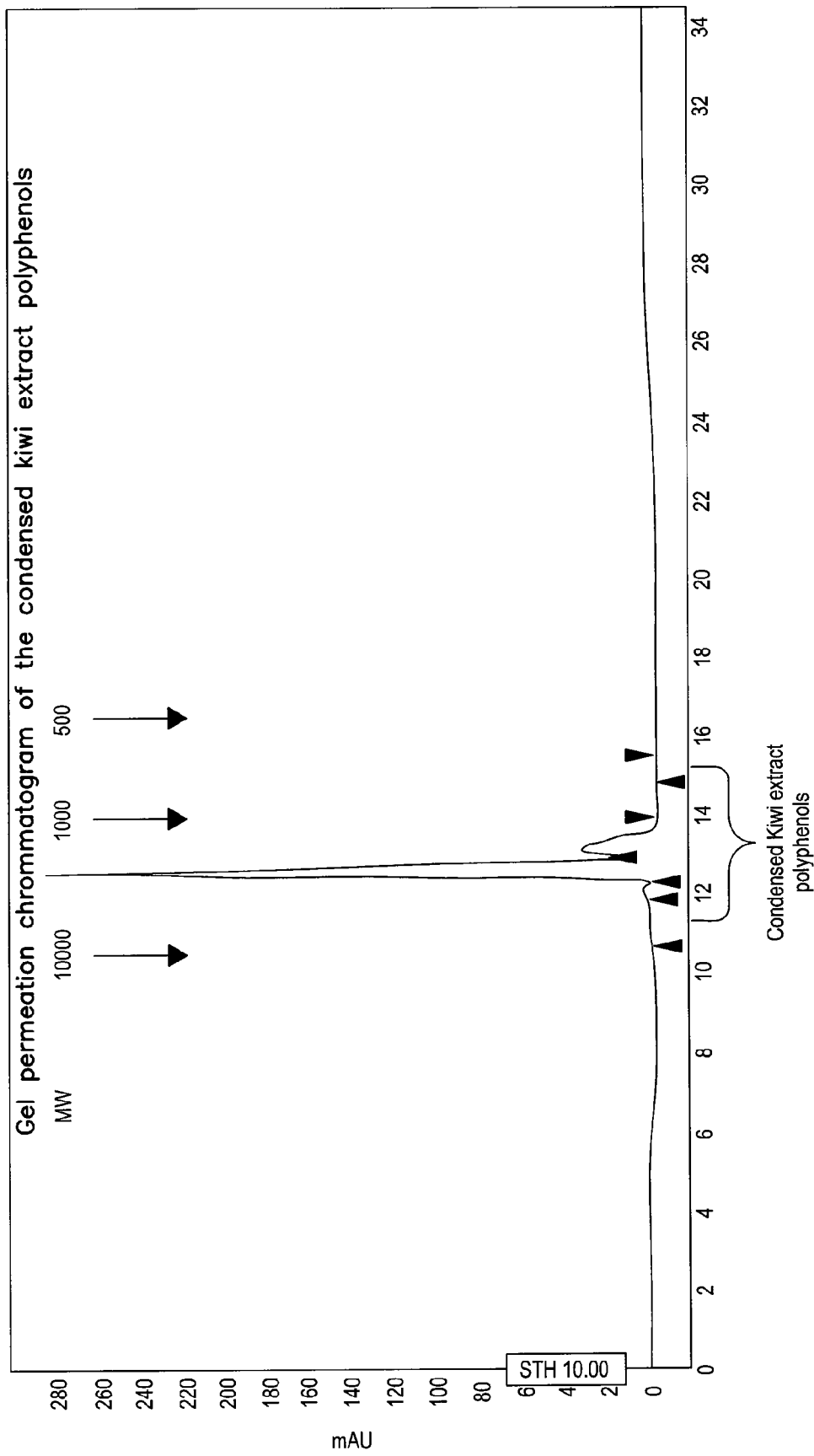
FIG. 11 is a gel permeation chromatogram of the condensed Kiwi extract polyphenol.

R'1 = R'2 = OH: Gallic Acid
R'1 = OH, R'2 = H: Dihydroxybenzoic Acid
R'1 = R'2 = H: p-Hydroxybenzoic Acid Based on HPLC investigations (size exclusion and reversed phase chromatography), the average molecular weight of the condensed kiwi extract polyphenols was estimated to about 3000, representing on average about 20 monomeric building blocks from the above given structures. (See FIGS. 10 and 11.)

Figure 16:
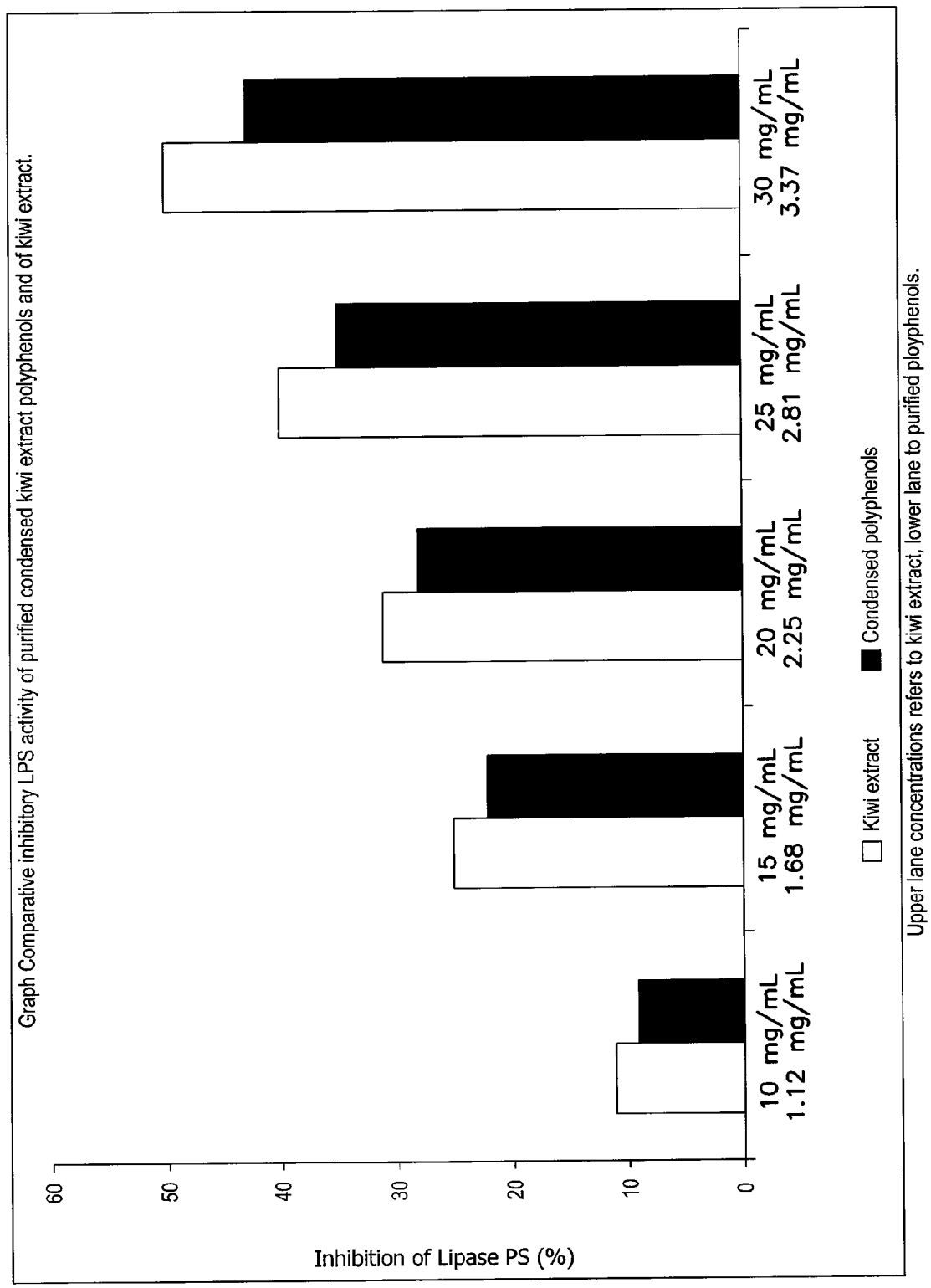
FIG. 16 is a graphical representation of the comparative inhibitory LPS activity of purified condensed Kiwi extract polyphenols and of Kiwi extract.

Biological Properties of Kiwi Extract:

As seen in FIG. 16, more than 90% of the inhibitory LPS activity of kiwi extract can most likely be attributed to the condensed kiwi extract polyphenols.

The enzyme fatty acid synthase I (FAS I) is an important enzyme participating in energy metabolism in-vivo In addition to the de-novo synthesis of palmitinic acid in the liver, FAS I activity was shown to be related to various human diseases. Recently, inhibition of FAS I was found to be associated with reduction of tumor growth and apoptosis of malignant cells.

Figure 12:
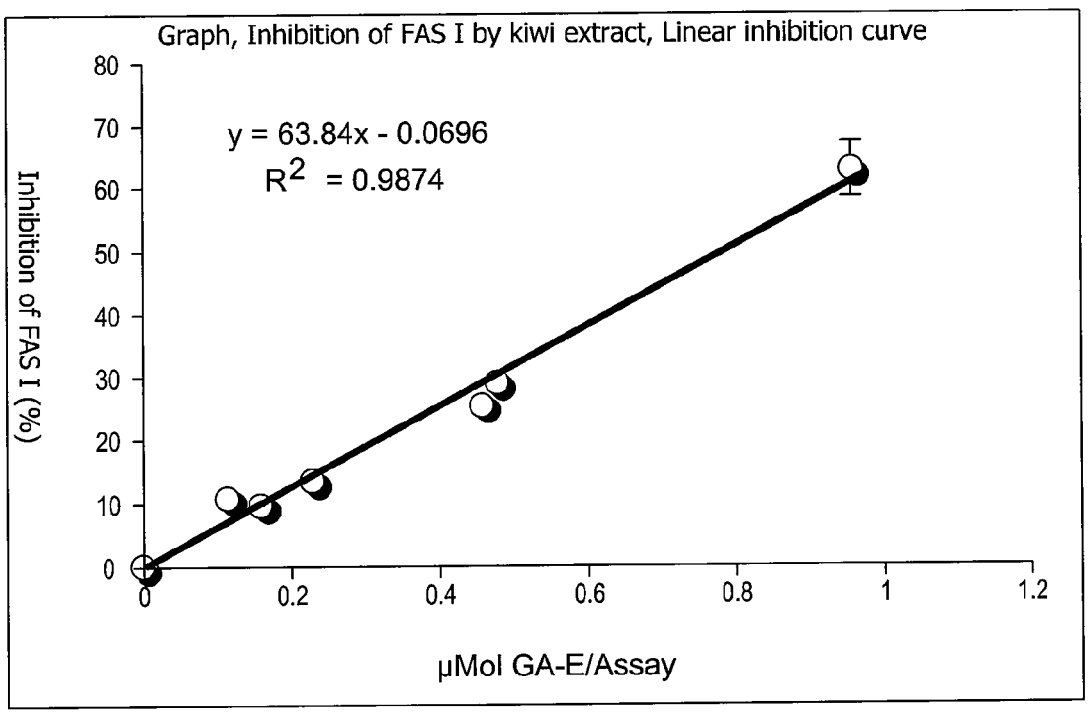
FIG. 12 is a graphical representation of the inhibition of FAS I by Kiwi extract, linear inhibition curve.
Figure 13:
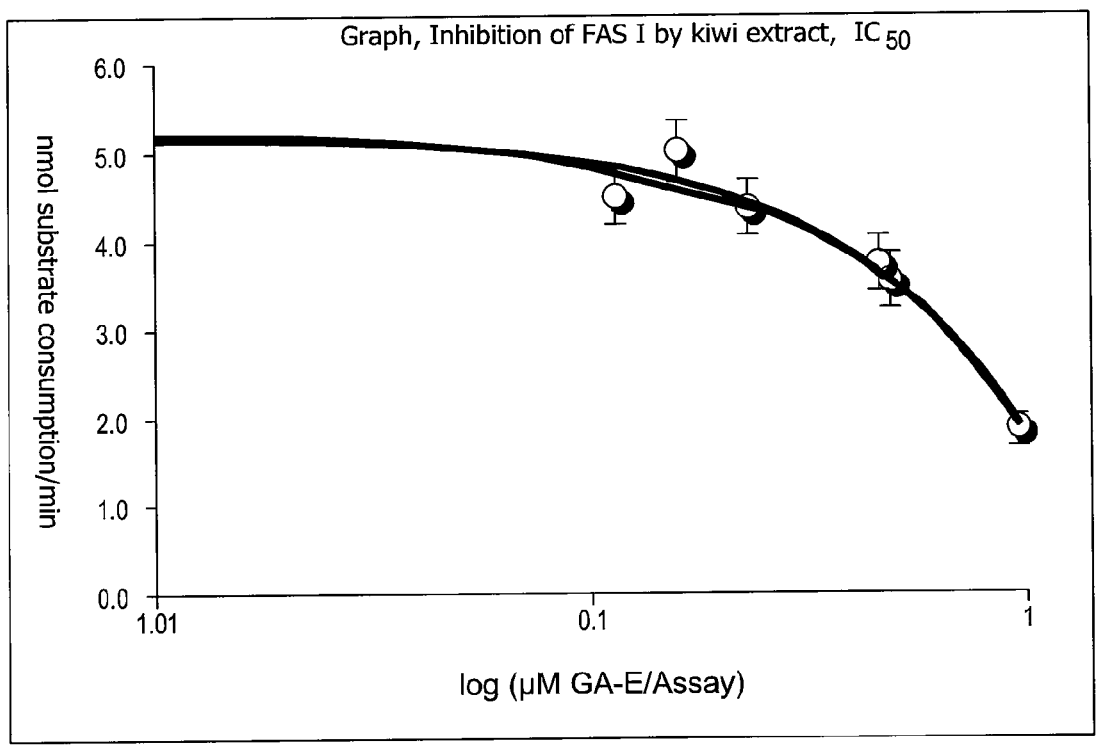
FIG. 13 is a graphical representation of inhibition of FAS I by Kiwi extract, $IC_{50}$.

Biological in-vitro testing of kiwi extract yielded substantial, dose dependent inhibition of FAS I. (See FIGS. 12 and 13.)

0.8 μmol GA-E in kiwi extract are sufficient to yield a 50% inhibition of the FAS I activity in the FAS Test assay described above. 0.8 μmol GA-E convert to 1.31 mg kiwi extract.

0.8 μmol GA-E in kiwi extract are sufficient to yield a 50% inhibition of the FAS I activity in the test assay (partly purified chicken liver proteins). 0.8 μmol GA-E converts to 1.31 mg kiwi extract.

Inhibition of Human Lipase (Pancreatic Source)

Human lipase of pancreatic source (LPS) is a key enzyme for digestion and absorption of triglycerides. The inhibition of LPS and, thereby, the prevention of lipolysis and absorption of fat is considered a successful approach to treat obesity.

Figure 14:
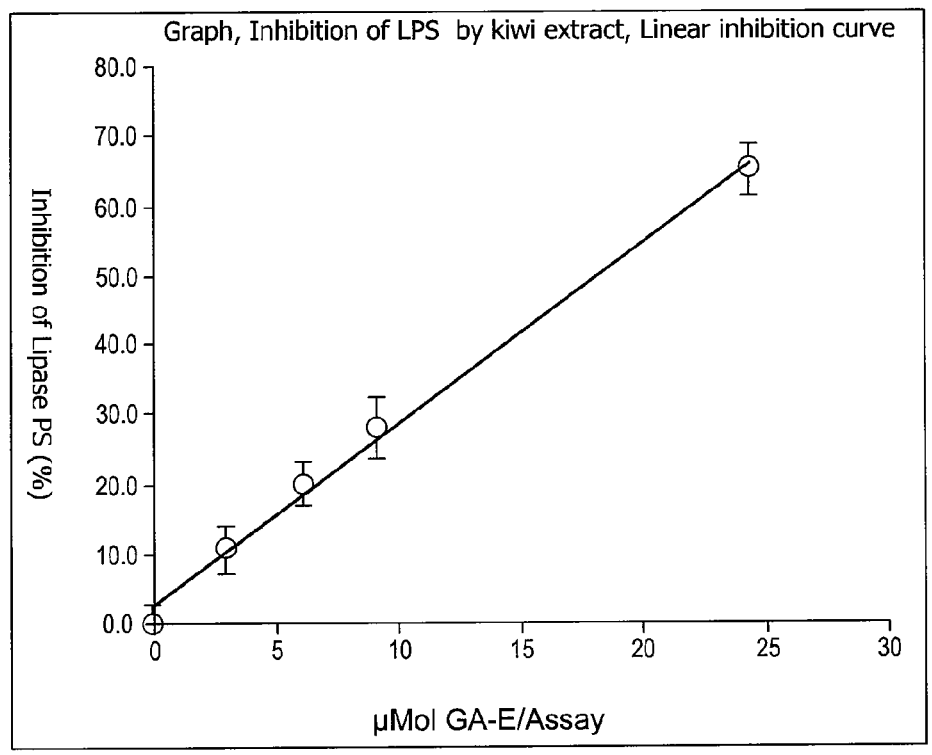
FIG. 14 is the graphical representation of the inhibition of LPS by Kiwi extract, linear inhibition curve.
Figure 15:
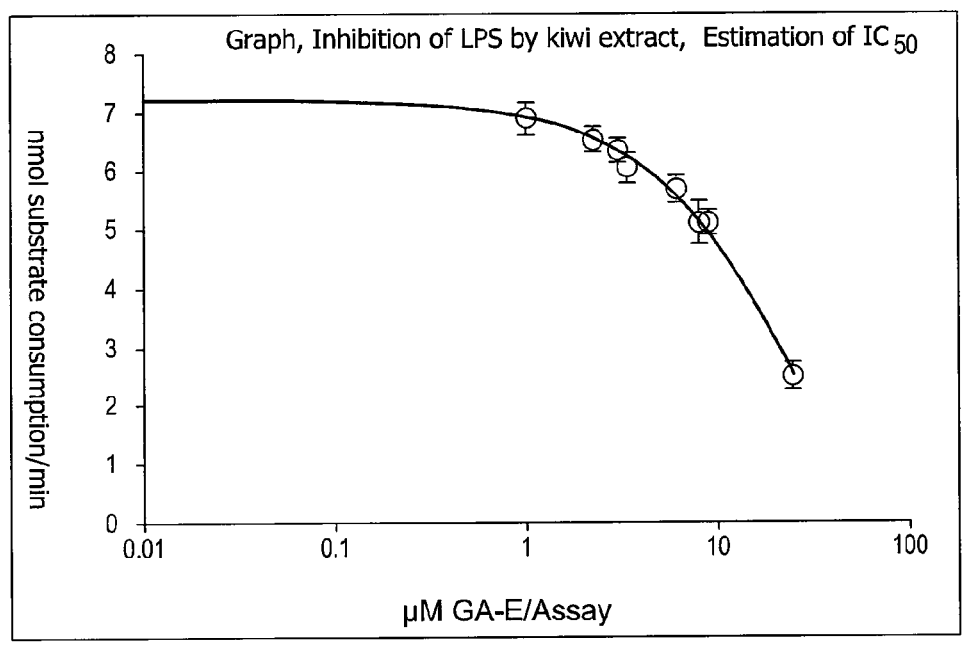
FIG. 15 is the graphical representation of LPS by Kiwi extract, Estimation of $IC_{50}$.

Biological in-vitro testing of kiwi extract yielded substantial, dose dependent inhibition of LPS by the Lipase Activity Test described above. (See FIGS. 14 and 15.)

18 μmol GA-E in kiwi extract are sufficient to yield a 50% inhibition of the LPS activity in the Lipase Activity Test assay (1 ml test system containing 0.3 IU lipase PS). 18 μmol GA-E converts to 30 mg kiwi extract.

Investigations with Purified Polyphenols from Kiwi Extract

The purified (as described for the Lipase Activity Test) condensed kiwi extract polyphenols were subjected to LPS inhibition testing to reveal their contribution to the activity of kiwi extract.

Considering a mass proportion of 11.25%, condensed kiwi extract polyphenols, preparations of 1.125-3.735 mg purified condensed polyphenols/ml were compared to 10-30 mg kiwi extract/ml test assay. (See FIG. 16.)

As seen in FIG. 16, more than 90% of the inhibitory LPS activity of kiwi extract can most likely be attributed to the condensed (conjugated) kiwi extract polyphenols.

Figure 17:
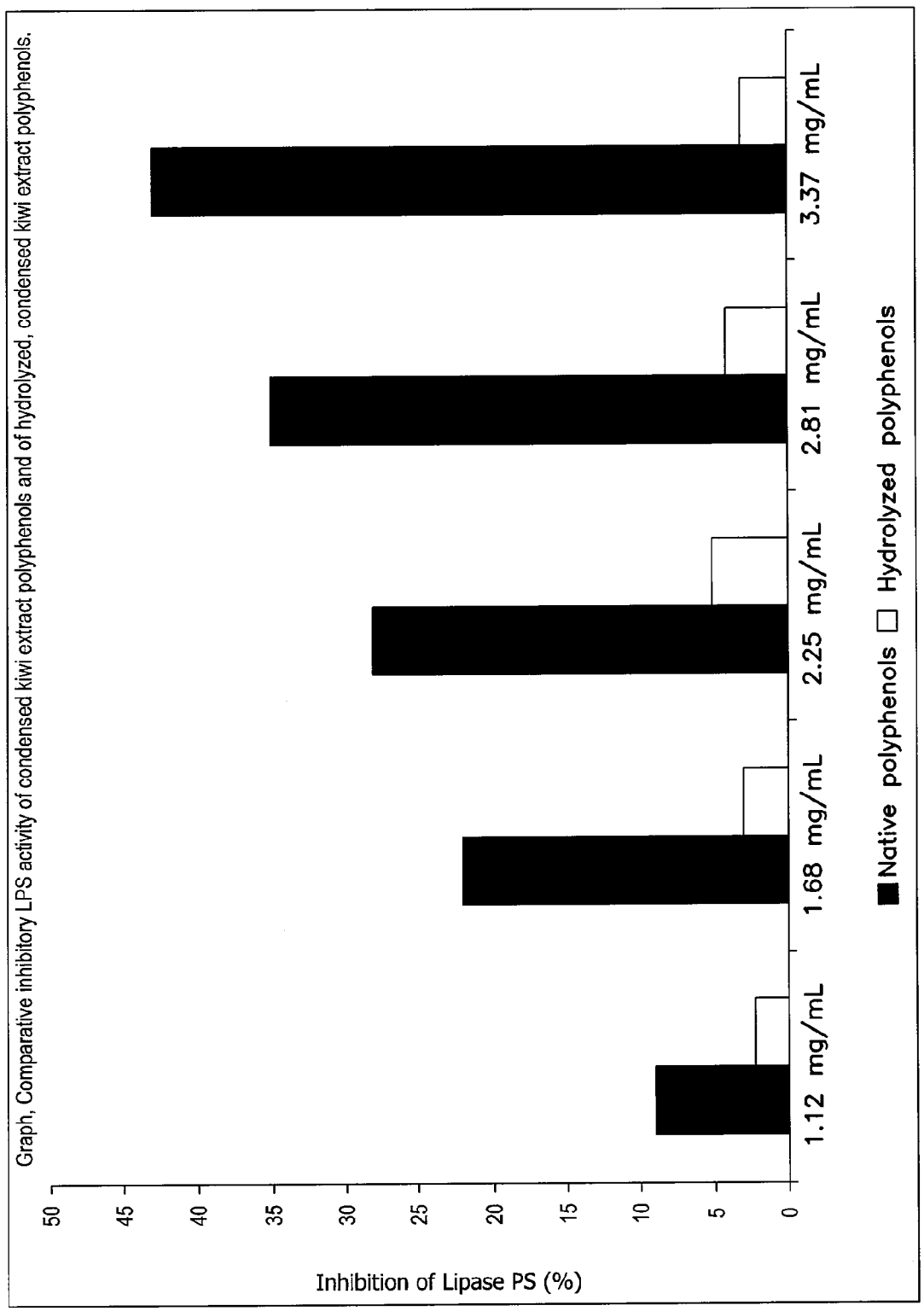
FIG. 17 is a graphical representation of the comparative inhibitory LPS activity of condensed Kiwi extract polyphenols and of hydrolyzed, condensed Kiwi extract polyphenols.

The purified condensed kiwi extract polyphenols were hydrolyzed and evaporated to dryness. After reconstitution in aqueous buffer, the hydrolysate was submitted to Lipase inhibition testing. Concentrations representing up to 3.3 mg of condensed kiwi extract polyphenols did not inhibit LPS after hydrolysis. (See FIG. 17.)

Calculation of Effective Dose:

60 μmol GA-E in Kiwi extract will inhibit 1 IU lipase by 50%. Considering a LPS activity of 50-100 IU/L gastric or ileal fluid 300-600 μmol GA-E are sufficient to block the LPS activity by 50%.

That converts to a dose of 0.5-1.0 g kiwi extract. Preferentially, kiwi extract should be taken prior to the ingestion of fat.

Protein Precipitation Assay:

The purified condensed kiwi extract polyphenols were tested for a protein precipitating potential.

0.15-1.0 mg bovine serum albumin (BSA) was dissolved in 1 ml aqueous buffer (reaction vials). To the reaction vials, between 0-0.5 mg purified polyphenols was added. After an incubation period of 30 minutes at 37~ C., the vials were centrifuged (15.000 rpm, 5 min.). The clear supernatant was subjected to a modified Micro-Lowry method (Total Protein Kit, Micro Lowry, Onishi & Barr Modification) for determination of the protein content according to the manual. As calibration range 0.15-1.0 mg BSA/ml was used.

In the range chosen, purified condensed kiwi extract polyphenols did not interact with BSA. In none of the incubated samples a loss of BSA was noted, indicating a polyphenols-protein interaction was observed.

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. An isolated kiwi extract comprising greater than about 10% by weight of a condensed polyphenolic derivative wherein the molecular weight of the polyphenolic derivative is between about 2,000 and about 4,000.

2. The isolated kiwi extract of claim 1, wherein the condensed polyphenolic derivative comprises a gallic acid derivative, a caffeic acid derivative and a catechin derivatives or mixtures thereof.

3. The isolated kiwi extract of claim 2, wherein the ratio of polyphenolic gallic acid derivative to polyphenolic catechin derivative is from about 1 to about 1 to about 10 to about 1.

4. The isolated kiwi extract of claim 2, wherein the ratio of polyphenolic caffeic acid derivative to polyphenolic catechin derivative is from about 1 to about 1 to about 10 to about 1.

5. The isolated kiwi extract of claim 2, wherein the ratio of polyphenolic gallic acid derivative, caffeic acid derivative and catechin derivative condensates are from about 1 to about 1 to about 1 to about 10 to about 10 to about 1.

6. The isolated kiwi extract of claim 2, wherein the polyphenolic gallic acid derivative is gallic acid, dihydroxybenzoic acid or p-hydroxybenzoic acid, the polyphenolic caffeic acid derivative is caffeic acid, coumaric acid or ferulic acid, the polyphenolic catechin derivative is catechin or gallocatechin, or mixtures thereof.

7. The isolated kiwi extract of claim 1, wherein the molecular weight of the condensed polyphenolic derivative is about 3,000.

8. The isolated kiwi extract of claim 2, wherein a degree of polymerization of the condensed polyphenolic derivative is between about 15 and about 25.

9. The isolated kiwi extract of claim 8, wherein the degree of polymerization of the condensed polyphenolic derivative is about 20.

10. The isolated kiwi extract of claim 1, wherein 1 gram of isolated kiwi extract contains from about 500 to about 700 μmol gallic acid equivalents.

11. The isolated kiwi extract of claim 1, wherein 1 gram of isolated kiwi extract contains from about 250 to about 400 μmol catechin equivalents.

12. A soft gelatin capsule comprising:
a soft gelatin capsule encapsulating an isolated kiwi extract comprising greater than about 10% by weight of a condensed polyphenolic derivative, wherein the molecular weight of the polyphenolic derivative is between about 2,000 and about 4,000.

13. A packaged formulation comprising:
a composition comprising an isolated kiwi extract comprising greater than about 10% by weight of a condensed polyphenolic derivative, wherein the molecular weight of the polyphenolic derivative is between about 2,000 and about 4,000; and
instructions for use thereof in a therapeutically effective manner to treat a disease or condition associated with a metabolic disorder.

14. The packaged formulation of claim 13, wherein, the metabolic disorder is obesity, hyperlipidemia, hypertension, arteriosclerosis, diabetes, laxation, constipation, fatty liver disease, colon cancer, prostate cancer, breast cancer, endometrium cancer or ovary carcinoma.

* * * * *